(12) United States Patent
Jeong et al.

(10) Patent No.: US 8,697,320 B2
(45) Date of Patent: Apr. 15, 2014

(54) PHENOL COMPOUNDS AND POSITIVE PHOTOSENSITIVE RESIN COMPOSITION INCLUDING THE SAME

(75) Inventors: Ji-Young Jeong, Uiwang-si (KR);
Min-Kook Chung, Uiwang-si (KR);
Hyun-Yong Cho, Uiwang-si (KR);
Yong-Sik Yoo, Uiwang-si (KR);
Jeong-Woo Lee, Uiwang-si (KR);
Jong-Hwa Lee, Uiwang-si (KR);
Hwan-Sung Cheon, Uiwang-si (KR);
Soo-Young Kim, Seongnam-si (KR);
Young-Ho Kim, Yongin-si (KR);
Jae-Hyun Kim, Yongin-si (KR); Su-Min Park, Seoul (KR)

(73) Assignees: Cheil Industries Inc., Gumi-si (KR);
Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 13/242,120

(22) Filed: Sep. 23, 2011

(65) Prior Publication Data

US 2012/0156614 A1    Jun. 21, 2012

(30) Foreign Application Priority Data

Dec. 15, 2010  (KR) .................. 10-2010-0128277

(51) Int. Cl.
*G03F 7/023* (2006.01)
*G03F 7/022* (2006.01)

(52) U.S. Cl.
CPC ............ *G03F 7/0226* (2013.01); *G03F 7/0233* (2013.01)
USPC ............. 430/18; 430/191; 430/192; 430/193; 430/288.1

(58) Field of Classification Search
CPC ....... C07C 69/88; C07C 69/92; G03F 7/0226; G03F 7/0233
USPC ................ 430/18, 165, 191, 192, 193, 281.1, 430/288.1
See application file for complete search history.

(56) References Cited

U.S. PATENT DOCUMENTS

| | | | |
|---|---|---|---|
| 2,772,975 A | 12/1956 | Rickers | |
| 2,797,213 A | 6/1957 | Moore | |
| 3,669,658 A | 6/1972 | Yonezawa et al. | |
| 4,289,699 A | 9/1981 | Oba et al. | |
| 4,400,521 A | 8/1983 | Oba et al. | |
| 5,077,378 A | 12/1991 | Mueller et al. | |
| 5,858,584 A | 1/1999 | Okabe et al. | |
| 6,143,467 A | 11/2000 | Hsu et al. | |
| 6,214,516 B1 | 4/2001 | Waterson et al. | |
| 6,593,043 B2 | 7/2003 | Suwa et al. | |
| 6,927,012 B2 | 8/2005 | Hatanaka et al. | |
| 6,927,013 B2 | 8/2005 | Banba et al. | |
| 6,929,890 B2 | 8/2005 | Miyoshi et al. | |
| 7,101,652 B2 | 9/2006 | Naiini et al. | |
| 7,129,011 B2 | 10/2006 | Rushkin et al. | |
| 7,238,455 B2 | 7/2007 | Banba et al. | |
| 7,255,972 B2 | 8/2007 | Nishiwaki et al. | |
| 7,361,445 B2 | 4/2008 | Banba et al. | |
| 7,416,822 B2 | 8/2008 | Kanada et al. | |
| 7,615,331 B2 | 11/2009 | Yamanaka et al. | |
| 7,687,208 B2 | 3/2010 | Shibui | |
| 8,080,350 B2 | 12/2011 | Banba et al. | |
| 8,088,882 B2 | 1/2012 | Sakayori | |
| 8,198,002 B2 | 6/2012 | Jung et al. | |
| 2002/0090564 A1 | 7/2002 | Suwa et al. | |
| 2004/0197703 A1 | 10/2004 | Miyoshi et al. | |
| 2004/0232393 A1* | 11/2004 | Do et al. ........................ | 252/582 |
| 2004/0253537 A1 | 12/2004 | Rushkin et al. | |
| 2006/0216441 A1 | 9/2006 | Schubel et al. | |
| 2007/0154843 A1 | 7/2007 | Kanada et al. | |
| 2009/0214860 A1 | 8/2009 | Enoki et al. | |
| 2010/0099043 A1 | 4/2010 | Jung et al. | |
| 2011/0003248 A1* | 1/2011 | Jung et al. ................. | 430/270.1 |
| 2011/0009506 A1 | 1/2011 | Lee et al. | |
| 2011/0111346 A1* | 5/2011 | Jeong et al. ................. | 430/286.1 |
| 2012/0156616 A1* | 6/2012 | Cho et al. ................... | 430/283.1 |

FOREIGN PATENT DOCUMENTS

| | | |
|---|---|---|
| CN | 1705914 A | 12/2005 |
| CN | 101727006 A | 6/2010 |
| EP | 0557991 A1 | 9/1993 |
| EP | 1491952 A2 | 12/2004 |
| EP | 1906246 A2 | 4/2008 |
| JP | 63-096162 | 4/1988 |
| JP | 07-281441 A | 10/1995 |
| JP | 09-302221 | 11/1997 |
| JP | 10-307393 | 11/1998 |
| JP | 11-338157 | 12/1999 |
| JP | 2000-292913 | 10/2000 |
| JP | 2001-215711 A | 8/2001 |
| JP | 2003-248314 | 9/2003 |

(Continued)

OTHER PUBLICATIONS

Office Action in commonly owned U.S. Appl. No. 12/834,933 mailed on Jun. 19, 2012, pp. 1-8.
International Search Report in commonly owned International Application No. PCT/KR2008/007906, dated Aug. 10, 2009, pp. 1-3.
International Written Opinion in commonly owned International Application No. PCT/KR2008/007906, dated Aug. 10, 2009, pp. 1-3.
Office Action in commonly owned U.S. Appl. No. 13/241,612 mailed on Oct. 3, 2012, pp. 1-9.
Office Action in commonly owned U.S. Appl. No. 12/884,316, mailed Jul. 6, 2012, pp. 1-8.

(Continued)

*Primary Examiner* — John Chu
(74) *Attorney, Agent, or Firm* — Additon, Higgins, Pendleton & Ashe, P.A.

(57) ABSTRACT

Disclosed are a novel phenol compound comprising a compound represented by Chemical Formula 1, a compound represented by Chemical Formula 2, or a combination thereof, and a positive photosensitive resin composition including the same.

16 Claims, No Drawings

(56) References Cited

FOREIGN PATENT DOCUMENTS

| | | |
|---|---|---|
| JP | 2006-071663 | 3/2006 |
| JP | 2006-091772 A | 4/2006 |
| JP | 2006-349700 A | 12/2006 |
| JP | 2007-017726 A | 1/2007 |
| JP | 2007-079264 A | 3/2007 |
| JP | 2007-176805 A | 7/2007 |
| JP | 2008-535003 | 8/2008 |
| JP | 2008-230984 | 10/2008 |
| JP | 2009-035495 | 2/2009 |
| JP | 2009-155481 A | 7/2009 |
| KR | 10-0264691 B | 9/2000 |
| KR | 10-2001-011635 A | 2/2001 |
| KR | 10-2002-0041302 A | 6/2002 |
| KR | 10-2003-0053471 A | 6/2003 |
| KR | 10-2004-0097880 A | 11/2004 |
| KR | 10-2006-0004908 A | 1/2006 |
| KR | 10-2008-0029919 A | 4/2008 |
| KR | 10-2008-040569 A | 5/2008 |
| KR | 10-2008-0053382 A | 6/2008 |
| KR | 10-2009-0097679 A | 9/2009 |
| KR | 10-2010-0042947 A | 4/2010 |
| KR | 10-2010-0053798 A | 5/2010 |
| KR | 10-2010-0080144 A | 7/2010 |
| KR | 10-2010-0110580 A | 10/2010 |
| TW | 200504464 | 2/2005 |
| TW | 200834240 | 8/2008 |
| WO | 2004/109400 A2 | 12/2004 |
| WO | 2006/104803 A2 | 10/2006 |
| WO | 2007/063721 A1 | 6/2007 |
| WO | 2008/020573 A1 | 2/2008 |
| WO | 2009/116724 A1 | 9/2009 |

OTHER PUBLICATIONS

Notice of Allowance in commonly owned U.S. Appl. No. 12/834,933, mailed Dec. 17, 2012, pp. 1-9.
Final Office Action in commonly owned U.S. Appl. No. 12/884,316, mailed Jan. 28, 2013, pp. 1-9.
Taiwanese Search Report in commonly owned Taiwanese Application No. 098143652 dated Jan. 2, 2013, pp. 1.
Chinese Search Report in commonly owned Chinese Application No. 2011103743252 dated Feb. 1, 2013, pp. 1-4.
Notice of Allowance in commonly owned U.S. Appl. No. 13/241,612 mailed Mar. 8, 2013, pp. 1-8.
Search Report in counterpart Chinese Application No. 201110374282.8 dated Nov. 27, 2013, pp. 1-2.
English translation of Search Report in counterpart Taiwanese Application No. 100142085 dated Sep. 13, 2013, pp. 1-2.
STN data cited in Office Action that issued on Nov. 18, 2013, in counterpart Korean Application No. 10-2010-0042947, pp. 1-8.

\* cited by examiner

PHENOL COMPOUNDS AND POSITIVE PHOTOSENSITIVE RESIN COMPOSITION INCLUDING THE SAME

CROSS-REFERENCE TO RELATED APPLICATION

This application claims priority under 35 USC Section 119 to and the benefit of Korean Patent Application No. 10-2010-0128277 filed in the Korean Intellectual Property Office on Dec. 15, 2010, the entire disclosure of which is incorporated herein by reference.

FIELD OF THE INVENTION

This disclosure relates to a novel phenol compound and a positive photosensitive resin composition including the same.

BACKGROUND OF THE INVENTION

The conventional surface protective layer and interlayer insulating layer for a semiconductor device includes a polyimide resin which can have excellent heat resistance, electrical properties, and mechanical properties.

The polyimide resin has recently been used as a photosensitive polyimide precursor composition which can be coated easily. The photosensitive polyimide precursor composition is coated on a semiconductor device, patterned by ultraviolet (UV) rays, developed, and heat imidized, to easily provide a surface protective layer, an interlayer insulating layer, and the like. Accordingly, it is possible to shorten the processing time compared with that of a conventional non-photosensitive polyimide precursor composition.

The photosensitive polyimide precursor composition can be applied as a positive type in which an exposed part is dissolved by development, or a negative type in which the exposed part is cured and maintained. Positive type compositions can be developed by a non-toxic alkali aqueous solution. The positive photosensitive polyimide precursor composition can include a polyimide precursor of polyamic acid, a photosensitive material of diazonaphthoquinone, and the like. However, it can be difficult to obtain a desired pattern using the positive photosensitive polyimide precursor composition because the carboxylic acid of the polyamic acid is too highly soluble in an alkali.

In order to solve this problem, a material to which a phenolic hydroxyl group has been introduced instead of carboxylic acid by esterifying polyamidic acid with an alcohol compound having at least one hydroxyl group has been proposed, but this material is insufficiently developed, causing problems of film loss or resin delamination from the substrate.

Recently, a material in which a polybenzoxazole precursor is mixed with a diazonaphthoquinone compound has drawn attention, but when the polybenzoxazole precursor composition is actually used, film loss of an unexposed part can be significantly increased, so it is difficult to obtain a desirable pattern after the developing process.

In order to improve this, if the molecular weight of the polybenzoxazole precursor is increased, the film loss amount of the unexposed part is reduced, but development residue (scum) is generated, so resolution may be decreased and the development duration on the exposed part may be increased.

In order to solve this problem, film loss may be suppressed in non-exposed parts during development by adding a certain phenol compound to a polybenzoxazole precursor composition. However, the effect of suppressing the film loss of the unexposed part is insufficient. Accordingly, there is still a need to increase the effects on suppressing film loss, along with preventing generation of the development residue (scum).

Furthermore, when this polyimide or polybenzoxazole precursor composition is prepared into a thermally cured film, the thermally cured film should have excellent mechanical properties such as tensile strength and elongation because it can remain in a semiconductor device as a surface protective layer. However, generally-used polyimide or polybenzoxazole precursors tend to have inappropriate mechanical properties, and in particular, elongation, and also have poor heat resistance.

In order to solve this problem, it has been reported that various additives can be added thereto or a precursor compound that is cross-linkable during the thermal curing can be used. However, while such compounds could improve mechanical properties, and in particular elongation, they could not accomplish optical properties such as sensitivity, resolution, and the like. Accordingly, there is still a need for research directed to methods that can attain excellent mechanical properties without deteriorating these optical properties.

SUMMARY OF THE INVENTION

One embodiment provides a novel phenol compound.

Another embodiment provides a positive photosensitive resin composition including the novel phenol compound, which can have excellent sensitivity, resolution, pattern formation properties, residue removal properties, mechanical properties, and reliability.

Yet another embodiment provides a photosensitive resin film fabricated by using the positive photosensitive resin composition.

Yet another embodiment provides a semiconductor device including the photosensitive resin film.

According to an embodiment, a novel phenol compound comprising the compound represented by the following Chemical Formula 1, the compound represented by the following Chemical Formula 2, or a combination thereof is provided.

[Chemical Formula 1]

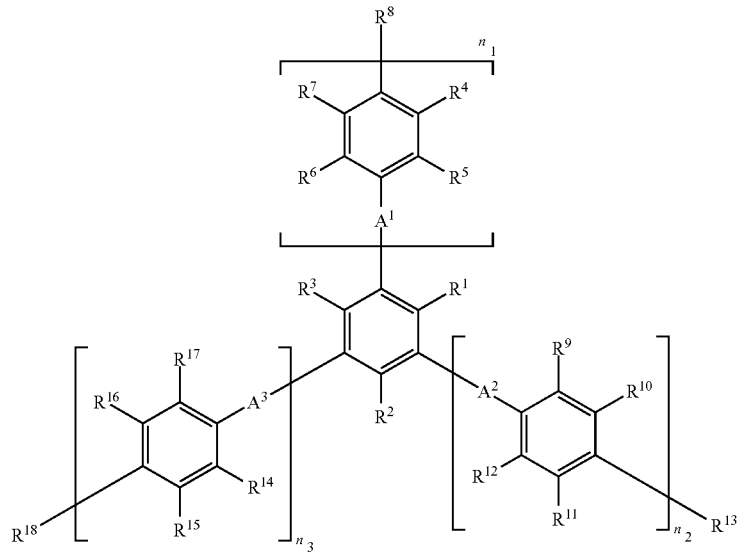

[Chemical Formula 2]

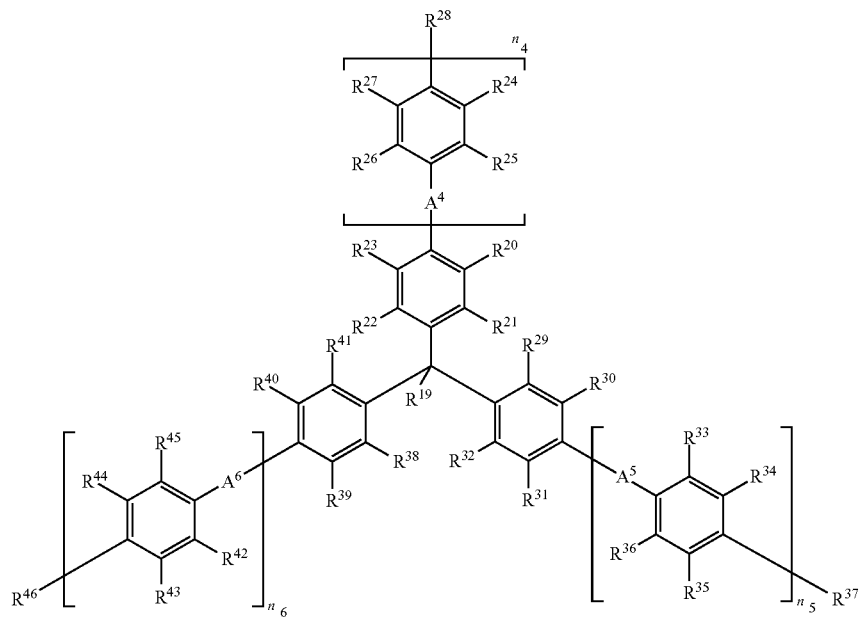

In Chemical Formulas 1 and 2, $R^1$ to $R^{46}$ are the same or different and are each independently hydrogen, hydroxyl, a substituted or unsubstituted C1 to C30 aliphatic organic group, substituted or unsubstituted C1 to C30 alkoxy, or halogen, provided that at least one of $R^1$ to $R^{46}$ is hydroxy, $A^1$ to $A^6$ are the same or different and are each independently O, CO, COO, $CR^{203}R^{204}$, $SO_2$, S, CONH (amide bond), $CH_2O$ or a single bond, wherein $R^{203}$ and $R^{204}$ are the same or different and are each independently hydrogen or a substituted or unsubstituted C1 to C30 aliphatic organic group, and $n_1$ to $n_6$ are the same or different and are each independently an integer ranging from 1 to 5.

The novel phenol compound may include 2 to 30 hydroxy groups.

The novel phenol compound may include a compound represented by one of the following Chemical Formulas 3 to 11, or a combination thereof.

[Chemical Formula 3]
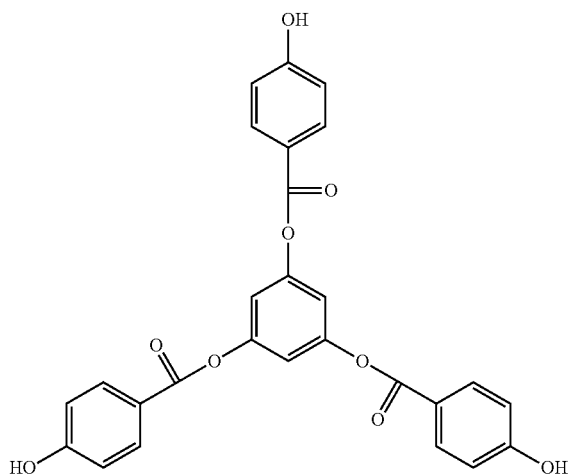
[Chemical Formula 4]
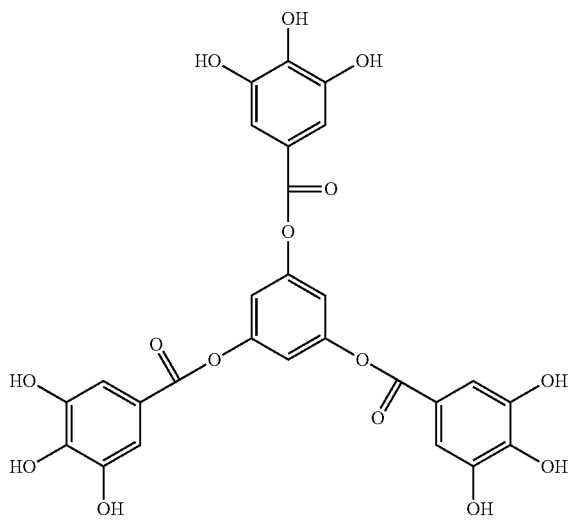
[Chemical Formula 5]
[Chemical Formula 6]
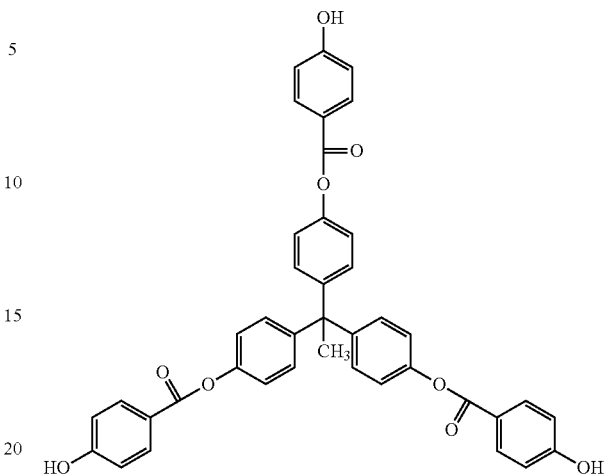
[Chemical Formula 7]
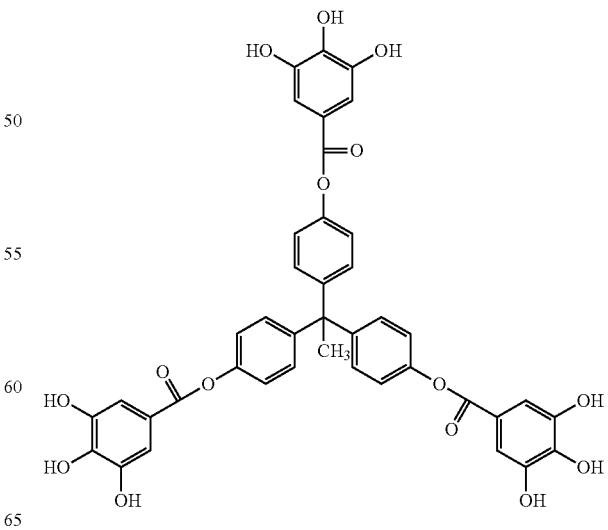
[Chemical Formula 8]

[Chemical Formula 9]

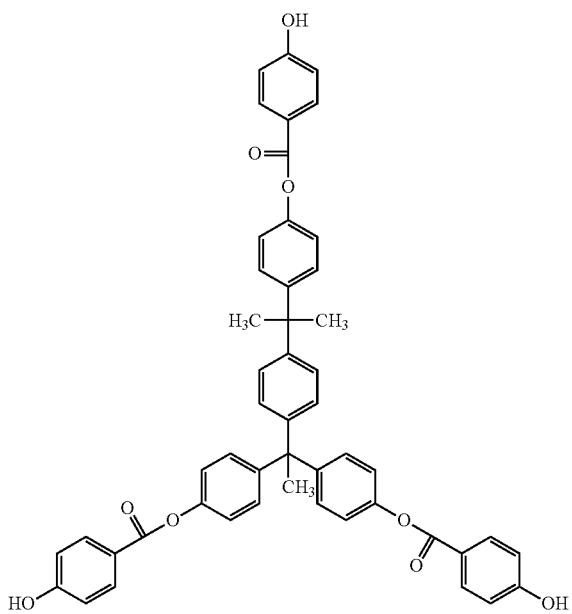

[Chemical Formula 10]

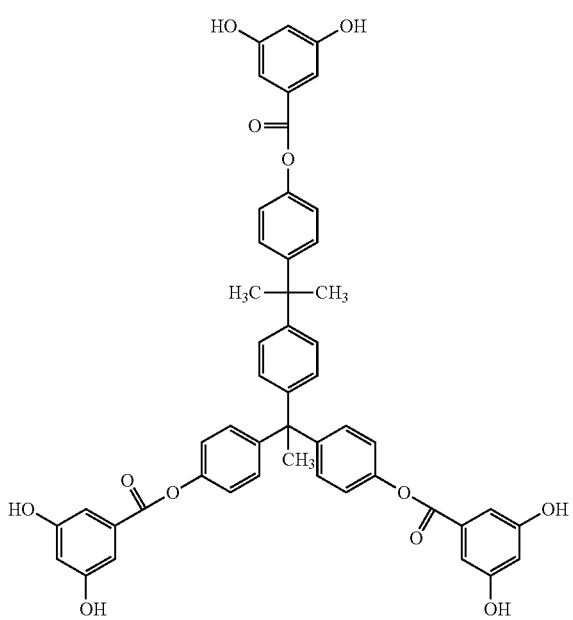

[Chemical Formula 11]

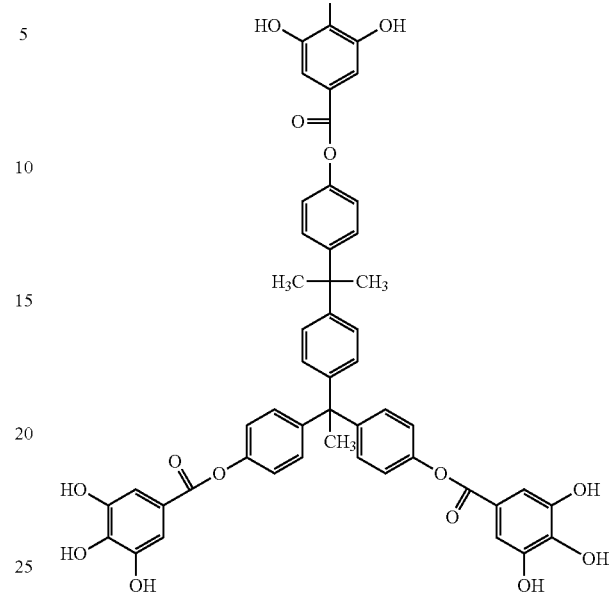

According to another embodiment, provided is a positive photosensitive resin composition that includes (A) a polybenzoxazole precursor including a repeating unit represented by the following Chemical Formula 12, a repeating unit represented by the following Chemical Formula 13, or a combination thereof, and a thermally polymerizable functional group at least one terminal end of the polybenzoxazole precursor; (B) a photosensitive diazoquinone compound; (C) the novel phenol compound; (D) a silane compound; and (E) a solvent.

[Chemical Formula 12]

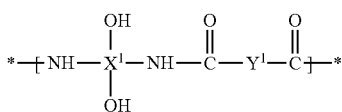

[Chemical Formula 13]

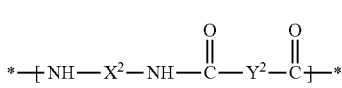

In Chemical Formulas 12 and 13, $X^1$ is an aromatic organic group, $X^2$ is an aromatic organic group, a divalent to hexavalent alicyclic organic group, or a functional group represented by the following Chemical Formula 14, and $Y^1$ and $Y^2$ are the same or different and are independently an aromatic organic group or a divalent to hexavalent alicyclic organic group,

[Chemical Formula 14]

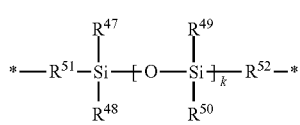

In Chemical Formula 14, $R^{47}$ to $R^{50}$ are the same or different and are each independently substituted or unsubstituted alkyl, substituted or unsubstituted aryl, substituted or unsubstituted alkoxy, or hydroxy, $R^{51}$ and $R^{52}$ are the same or different and are each independently substituted or unsubstituted alkylene or substituted or unsubstituted arylene, and k is an integer ranging from 1 to 50.

The thermally polymerizable functional group may be derived from a reactive end-capping monomer selected from monoamines, monoanhydrides, or monocarboxylic acid halides including a carbon-carbon multiple bond.

Examples of the monoamines include without limitation toluidine, dimethylaniline, ethylaniline, aminophenol, aminobenzylalcohol, aminoindan, aminoacetophenone, and the like, and combinations thereof. Examples of the monoanhydrides include without limitation 5-norbornene-2,3-dicarboxylanhydride represented by the following Chemical Formula 24, 3,6-epoxy-1,2,3,6-tetra hydrophthalicanhydride represented by the following Chemical Formula 25, isobutenyl succinic anhydride represented by the following Chemical Formula 26, maleic anhydride, aconitic anhydride, 3,4,5,6-tetrahydrophthalic anhydride, cis-1,2,3,6,-tetrahydrophthalic anhydride, itaconic anhydride (IA), citraconic anhydride (CA), 2,3-dimethylmaleic anhydride (DMMA), and the like, and combinations thereof.

[Chemical Formula 24]

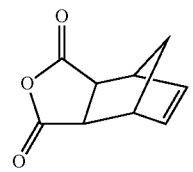

[Chemical Formula 25]

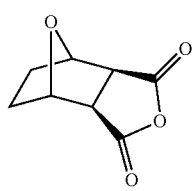

[Chemical Formula 26]

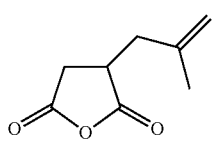

The monocarboxylic acid halides including the carbon-carbon multiple bond may be represented by the following Chemical Formula 31.

[Chemical Formula 31]

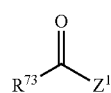

In Chemical Formula 31, $R^{73}$ is a substituted or unsubstituted alicyclic organic group or a substituted or unsubstituted aromatic organic group, and $Z^1$ is F, Cl, Br, or I.

Examples of the monocarboxylic acid halides including a carbon-carbon multiple bond include without limitation 5-norbornene-2-carboxylic acid halide represented by the following Chemical Formula 32, 4-nadimido benzoylhalide represented by the following Chemical Formula 33, 4-(4-phenylethynylphthalimido)benzoylhalide represented by the following Chemical Formula 34, 4-(2-phenylmaleicimido) benzoylhalide represented by the following Chemical Formula 35, benzoylhalide represented by the following Chemical Formula 36, cyclobenzoylhalide represented by the following Chemical Formula 37, 4-(3-phenylethynylphthalimido)benzoylhalide, 4-maleimido benzoylhalide, and the like, and combinations thereof.

[Chemical Formula 32]

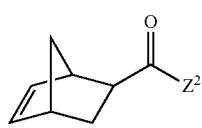

[Chemical Formula 33]

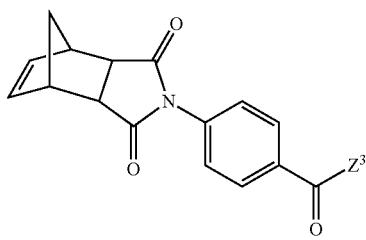

[Chemical Formula 34]

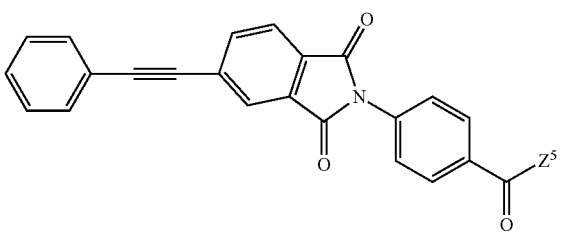

[Chemical Formula 35]

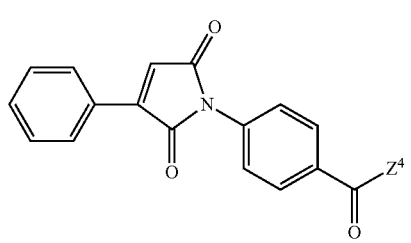

[Chemical Formula 36]

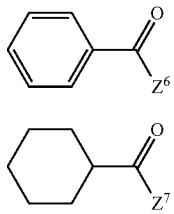

[Chemical Formula 37]

In Chemical Formulas 32 to 37, $Z^2$ to $Z^7$ are the same or different and are each independently F, Cl, Br, or I.

When the polybenzoxazole precursor includes a combination of a repeating unit represented by the above Chemical Formula 12 and a repeating unit represented by the above Chemical Formula 13, and the total amount of a repeating unit represented by above Chemical Formula 12 and a repeating unit represented by the above Chemical Formula 13 is 100 mol %, a repeating unit represented by above Chemical Formula 12 may be included in an amount ranging from about 60 mol % to about 95 mol % and a repeating unit represented by the above Chemical Formula 13 may be included in an amount ranging from about 5 mol % to about 40 mol %.

The polybenzoxazole precursor may have a weight average molecular weight (Mw) ranging from about 3000 to about 300,000.

The positive photosensitive resin composition may include about 5 to about 100 parts by weight of the photosensitive diazoquinone compound (B), about 1 to about 30 parts by weight of the novel phenol compound (C), about 0.1 to about 30 parts by weight of the silane compound (D), and about 50 to about 300 parts by weight of the solvent (E), wherein the amounts of (B), (C), (D), and (E) are based on about 100 parts by weight of the polybenzoxazole precursor (A).

According to another embodiment, a photosensitive resin film fabricated using the positive photosensitive resin composition is provided.

According to a further embodiment, a semiconductor device including the photosensitive resin film is provided.

Hereinafter, further embodiments will be described in detail.

The positive photosensitive resin composition includes the novel phenol compound being capable of promoting developability for an alkali development solution as a dissolution promoting agent, and thus may improve mechanical properties and reliability of a film, and provide excellent sensitivity, resolution, pattern formation properties, and residue removal properties, high elongation, high tensile strength, and low film shrinkage.

DETAILED DESCRIPTION

The present invention will be described more fully hereinafter in the following detailed description of the invention, in which some but not all embodiments of the invention are described. Indeed, this invention may be embodied in many different forms and should not be construed as limited to the embodiments set forth herein; rather, these embodiments are provided so that this disclosure will satisfy applicable legal requirements.

As used herein, when a specific definition is not otherwise provided, the term "substituted" refers to one substituted with at least a substituent comprising halogen (F, Cl, Br or I), hydroxy, nitro, cyano, amino ($NH_2$, $NH(R^{200})$, or $N(R^{201})(R^{202})$), wherein $R^{200}$, $R^{201}$ and $R^{202}$ are the same or different and are independently C1 to C10 alkyl), amidino, hydrazine, hydrazone, carboxyl, substituted or unsubstituted alkyl, a substituted or unsubstituted alicyclic organic group, substituted or unsubstituted aryl, substituted or unsubstituted alkenyl, substituted or unsubstituted alkynyl, substituted or unsubstituted heteroaryl, a substituted or unsubstituted heterocyclic group, or a combination thereof, in place of at least one hydrogen of a functional group.

As used herein, when a specific definition is not otherwise provided, the term "alkyl" refers to C1 to C30 alkyl, for example C1 to C15 alkyl, the term "cycloalkyl" refers to C3 to C30 cycloalkyl, for example C3 to C18 cycloalkyl, the term "alkoxy" refers to C1 to C30 alkoxy, for example C1 to C18 alkoxy, the term "aryl" refers to C6 to C30 aryl, for example C6 to C18 aryl, the term "alkenyl" refers to C2 to C30 alkenyl, for example C2 to C18 alkenyl, the term "alkylene" refers to C1 to C30 alkylene, for example C1 to C18 alkylene, the term "alkynyl" refers to C2 to C30 alkynyl, for example C2 to C16 alkynyl, the term "arylene" refers to C6 to C30 arylene, for example C6 to C18 arylene, the term "heteroaryl" refers to C2 to C30 heteroaryl, for example C1 to C16 heteroaryl, and the term "heterocyclic" refers to C2 to C30 heterocyclic, for example C2 to C18 heterocyclic.

As used herein, when a specific definition is not otherwise provided, the term "aliphatic organic group" refers to C1 to C30 alkyl, C2 to C30 alkenyl, C2 to C30 alkynyl, C1 to C30 alkylene, C2 to C30 alkenylene, or C2 to C30 alkynylene, for example C1 to C15 alkyl, C2 to C15 alkenyl, C2 to C15 alkynyl, C1 to C15 alkylene, C2 to C15 alkenylene, or C2 to C15 alkynylene, the term "alicyclic organic group" refers to C3 to C30 cycloalkyl, C3 to C30 cycloalkenyl, C3 to C30 cycloalkynyl, C3 to C30 cycloalkylene, C3 to C30 cycloalkenylene, or C3 to C30 cycloalkynylene, for example C3 to C15 cycloalkyl, C3 to C15 cycloalkenyl, C3 to C15 cycloalkynyl, C3 to C15 cycloalkylene, C3 to C15 cycloalkenylene, or C3 to C15 cycloalkynylene, and the term "aromatic organic group" refers to C6 to C30 aryl, C2 to C30 heteroaryl, C6 to C30 arylene, or C2 to C30 heteroarylene, for example C6 to C16 aryl, C2 to C16 heteroaryl, C6 to C16 arylene, or C2 to C16 heteroarylene.

As used herein, when a specific definition is not otherwise provided, the term "hetero" may refer to one including at least one heteroatom of N, O, S, P, or a combination thereof in place of a carbon ring atom.

As used herein, when a specific definition is not otherwise provided, the term "combination" refers to mixing or copolymerization. Also, the term "copolymerization" refers to block copolymerization or random copolymerization, and the term "copolymer" refers to a block copolymer or a random copolymer.

Also, "*" refers to a linking part between the same or different atoms, or chemical Formulas.

According to one embodiment, the novel phenol compound comprises a compound represented by the following Chemical Formula 1, a compound represented by the following Chemical Formula 2, or a combination thereof.

[Chemical Formula 1]

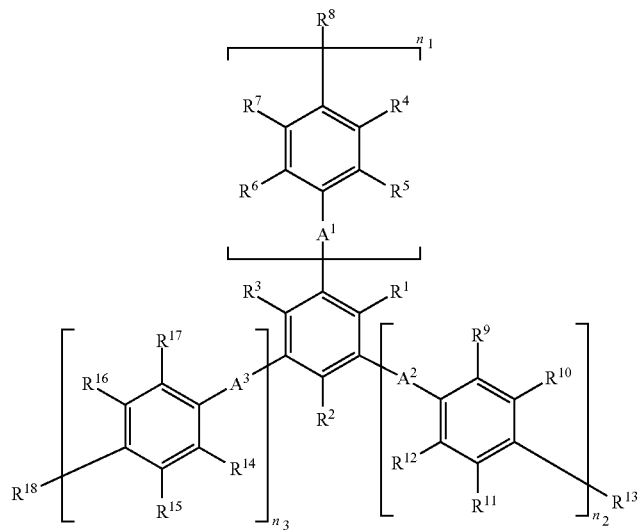

[Chemical Formula 2]

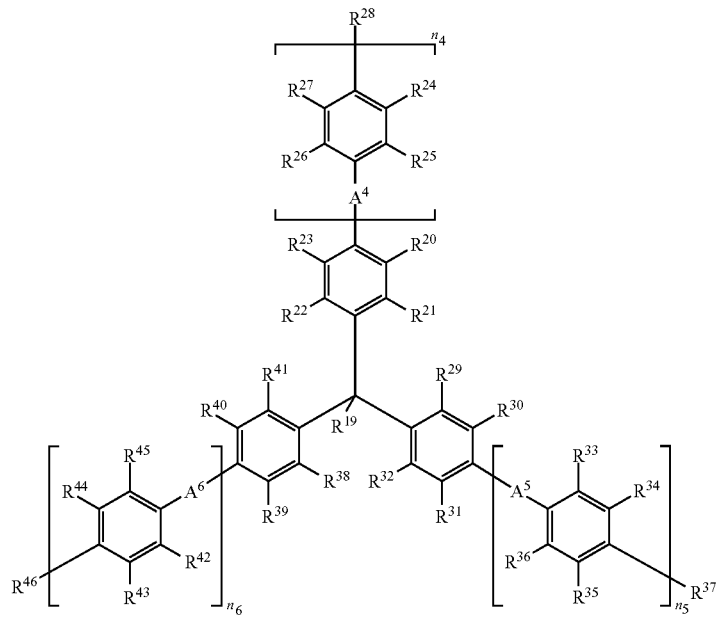

In Chemical Formulas 1 and 2, $R^1$ to $R^{46}$ are the same or different and are each independently hydrogen, hydroxyl, a substituted or unsubstituted C1 to C30 aliphatic organic group, substituted or unsubstituted C1 to C30 alkoxy, or halogen, provided that at least one of $R^1$ to $R^{46}$ is hydroxy, $A^1$ to $A^6$ are the same or different and are each independently O, CO, COO, $CR^{203}R^{204}$, $SO_2$, S, CONH (amide bond), $CH_2O$ or a single bond, wherein $R^{203}$ and $R^{204}$ are the same or different and are each independently hydrogen or a substituted or unsubstituted C1 to C30 aliphatic organic group, $n_1$ to $n_6$ are the same or different and are each independently an integer ranging from 1 to 5, for example 1 to 3, and as another example 1 or 2.

The novel phenol compound may be used as one component of a positive photosensitive resin composition. This may be described in more detail.

Specifically, the novel phenol compound may include a compound represented by one of the following Chemical Formulas 3 to 11, or a combination thereof.

[Chemical Formula 3]
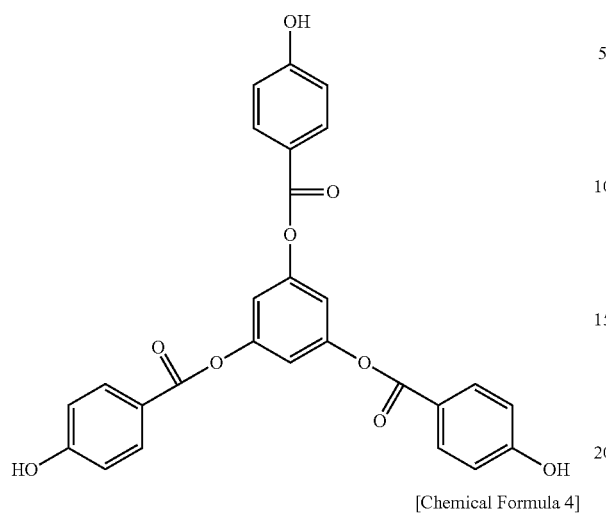
[Chemical Formula 4]
[Chemical Formula 5]
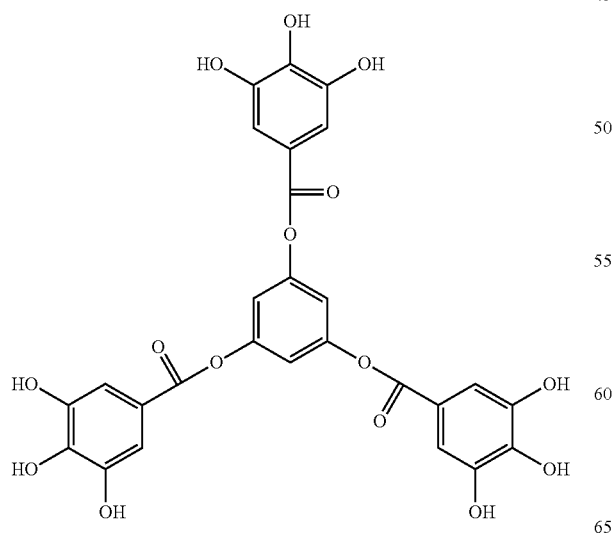
[Chemical Formula 6]
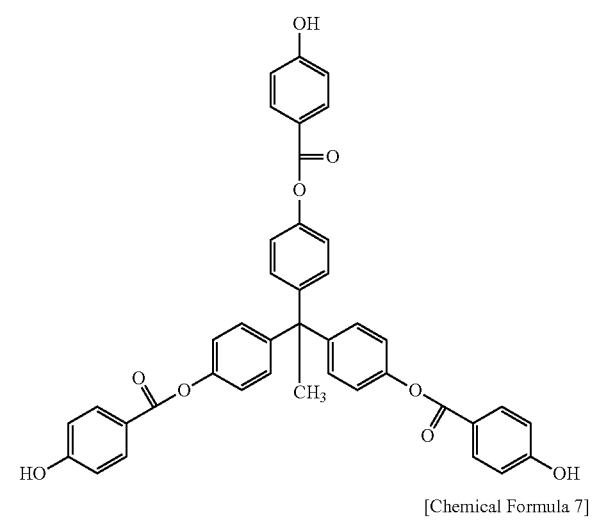
[Chemical Formula 7]
[Chemical Formula 8]

[Chemical Formula 9]

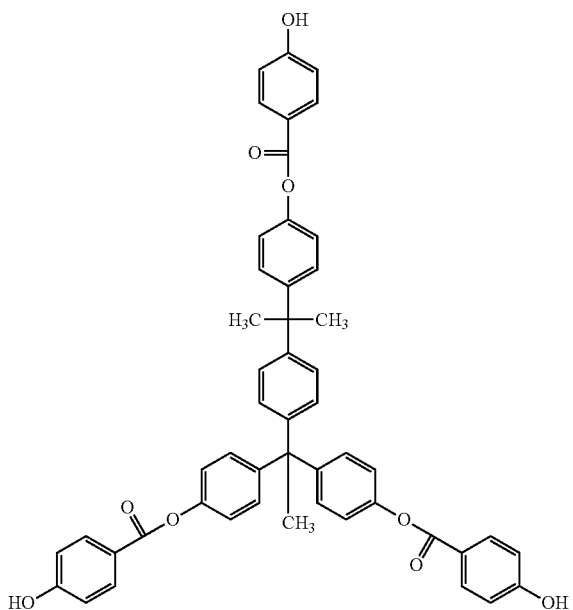

[Chemical Formula 10]

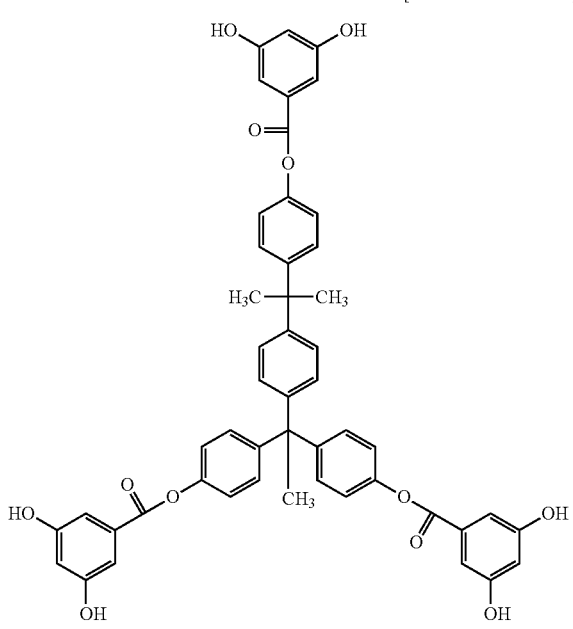

[Chemical Formula 11]

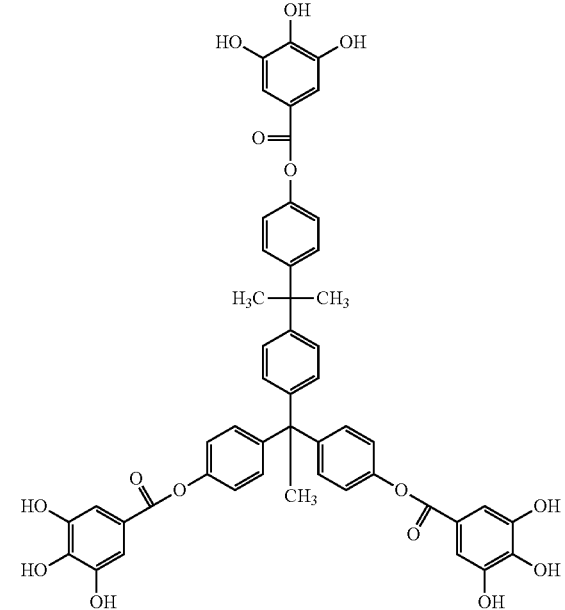

According to another embodiment, provided is a positive photosensitive resin composition that included (A) a polybenzoxazole precursor including a repeating unit represented by the following Chemical Formula 12, a repeating unit represented by the following Chemical Formula 13, or a combination thereof, and a thermally polymerizable functional group at least one terminal end of the polybenzoxazole precursor; (B) a photosensitive diazoquinone compound; (C) the novel phenol compound; (D) a silane compound; and (E) a solvent.

[Chemical Formula 12]

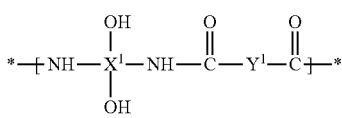

[Chemical Formula 13]

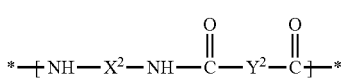

In Chemical Formulas 12 and 13, $X^1$ is an aromatic organic group, $X^2$ is an aromatic organic group, a divalent to hexavalent alicyclic organic group, or a functional group represented by the following Chemical Formula 14, and $Y^1$ and $Y^2$ are the same or different and are independently an aromatic organic group or a divalent to hexavalent alicyclic organic group.

[Chemical Formula 14]

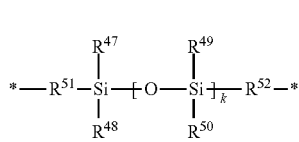

In Chemical Formula 14, $R^{47}$ to $R^{50}$ are the same or different and are each independently substituted or unsubstituted alkyl, substituted or unsubstituted aryl, substituted or unsubstituted alkoxy, or hydroxy, $R^{51}$ and $R^{52}$ are the same or different and are each independently substituted or unsubstituted alkylene or substituted or unsubstituted arylene, and k is an integer ranging from 1 to 50.

The positive photosensitive resin composition may include an additional additive (F).

Hereinafter, each composition component is described in detail.

(A) Polybenzoxazole Precursor

The polybenzoxazole precursor includes a repeating unit represented by the above Chemical Formula 12, a repeating unit represented by the above Chemical Formula 13, or a combination thereof, and a thermally polymerizable functional group at least one terminal end of the polybenzoxazole precursor.

In the above Chemical Formula 12, $X^1$ may be an aromatic organic group.

$X^1$ may be a residual group derived from an aromatic diamine.

Examples of the aromatic diamine may include without limitation 3,3'-diamino-4,4'-dihydroxybiphenyl, 4,4'-diamino-3,3'-dihydroxybiphenyl, bis(3-amino-4-hydroxyphenyl)propane, bis(4-amino-3-hydroxyphenyl)propane, bis(3-amino-4-hydroxyphenyl)sulfone, bis(4-amino-3-hydroxyphenyl)sulfone, 2,2-bis(3-amino-4-hydroxyphenyl)-1,1,1,3,3,3-hexafluoropropane, 2,2-bis(4-amino-3-hydroxyphenyl)-1,1,1,3,3,3-hexafluoropropane,
2,2-bis(3-amino-4-hydroxy-5-trifluoromethylphenyl) hexafluoropropane,
2,2-bis(3-amino-4-hydroxy-6-trifluoromethylphenyl) hexafluoropropane,
2,2-bis(3-amino-4-hydroxy-2-trifluoromethylphenyl) hexafluoropropane,
2,2-bis(4-amino-3-hydroxy-5-trifluoromethylphenyl) hexafluoropropane,
2,2-bis(4-amino-3-hydroxy-6-trifluoromethylphenyl) hexafluoropropane,
2,2-bis(4-amino-3-hydroxy-2-trifluoromethylphenyl) hexafluoropropane,
2,2-bis(3-amino-4-hydroxy-5-pentafluoroethylphenyl) hexafluoropropane,
2-(3-amino-4-hydroxy-5-trifluoromethylphenyl)-2-(3-amino-4-hydroxy-5-pentafluoroethylphenyl)hexafluoropropane,
2-(3-amino-4-hydroxy-5-trifluoromethyl phenyl)-2-(3-hydroxy-4-amino-5-trifluoro-methylphenyl)hexafluoropropane,
2-(3-amino-4-hydroxy-5-trifluoromethylphenyl)-2-(3-hydroxy-4-amino-6-trifluoro-methylphenyl)hexafluoropropane,
2-(3-amino-4-hydroxy-5-trifluoromethylphenyl)-2-(3-hydroxy-4-amino-2-trifluoro-methylphenyl)hexafluoropropane,
2-(3-amino-4-hydroxy-2-trifluoromethylphenyl)-2-(3-hydroxy-4-amino-5-trifluoro-methylphenyl)hexafluoropropane,
2-(3-amino-4-hydroxy-6-trifluoromethylphenyl)-2-(3-hydroxy-4-amino-5-trifluoro-methylphenyl)hexafluoropropane,
and the like, and combinations thereof.

$X^1$ may include a functional group represented by the following Chemical Formulas 15 and 16, but is not limited thereto.

[Chemical Formula 15]

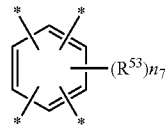

[Chemical Formula 16]

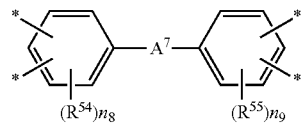

In Chemical Formulas 15 and 16, $A^7$ is O, CO, $CR^{205}R^{206}$, $SO_2$, S or a single bond, wherein $R^{205}$ and $R^{206}$ are the same or different and are each independently hydrogen or substituted or unsubstituted alkyl, for example fluoroalkyl, $R^{53}$ to $R^{55}$ are the same or different and are each independently hydrogen, substituted or unsubstituted alkyl, hydroxy, carboxyl, or thiol, $n_7$ is an integer ranging from 1 or 2, and $n_8$ and $n_9$ are the same or different and are independently integers ranging from 1 to 3.

In Chemical Formula 13, $X^2$ is an aromatic organic group, a divalent to hexavalent alicyclic organic group, or a functional group represented by the above Chemical Formula 14

$X^2$ may be a residual group derived from an aromatic diamine, an alicyclic diamine, or a silicon diamine.

Examples of the aromatic diamine include without limitation 3,4'-diaminodiphenylether, 4,4'-diaminodiphenylether, 3,4'-diaminodiphenylmethane, 4,4'-diaminodiphenylmethane, 4,4'-diaminodiphenylsulfone, 4,4'-diaminodiphenylsulfide, benzidine, m-phenylenediamine, p-phenylenediamine, 1,5-naphthalenediamine, 2,6-naphthalenediamine, bis(4-aminophenoxyphenyl)sulfone, bis(3-aminophenoxyphenyl)sulfone, bis(4-aminophenoxy)biphenyl, bis[4-(4-aminophenoxy)phenyl]ether, 1,4-bis(4-aminophenoxy)benzene, compounds with the aromatic ring substituted with an alkyl group or a halogen atom, and the like, and combinations thereof.

Examples of the silicon diamine include without limitation bis(4-aminophenyl)dimethylsilane, bis(4-aminophenyl)tetramethylsiloxane, bis(p-aminophenyl)tetramethyldisiloxane, bis(γ-aminopropyl)tetramethyldisiloxane, 1,4-bis(γ-aminopropyldimethylsilyl)benzene, bis(4-aminobutyl) tetramethyldisiloxane, bis(γ-aminopropyl) tetraphenyldisiloxane, 1,3-bis(aminopropyl) tetramethyldisiloxane, and the like, and combinations thereof.

Examples of the alicyclic diamine include without limitation 1,4-diaminocyclohexane, 1,3-diaminocyclohexane, 1,2-diaminocyclohexane, 4,4'-methylenebiscyclohexylamine, 4,4'-methylenebis (2-methylcyclohexylamine), and the like, and combination thereof.

Examples of the $X^2$ include a functional group represented by the following Chemical Formulas 17 to 20, but are not limited thereto.

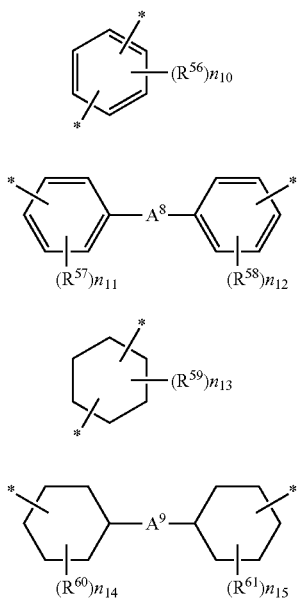

[Chemical Formula 17]

[Chemical Formula 18]

[Chemical Formula 19]

[Chemical Formula 20]

In Chemical Formulas 17 to 20, $A^8$ and $A^9$ are the same or different and are each independently O, CO, $CR^{207}R^{208}$, $SO_2$, S or a single bond, wherein $R^{207}$ and $R^{208}$ are the same or different and are each independently hydrogen or substituted or unsubstituted alkyl, for example fluoroalkyl, $R^{56}$ to $R^{61}$ are the same or different and are each independently hydrogen, substituted or unsubstituted alkyl, hydroxy, carboxyl, or thiol, $n_{10}$ and $n_{13}$ are the same or different and are each independently integers ranging from 1 to 4, and $n_{11}$, $n_{12}$, $n_{14}$ and $n_{15}$ are the same or different and are each independently integers ranging from 1 to 5.

In Chemical Formulas 12 and 13, $Y^1$ and $Y^2$ are the same or different and are each independently an aromatic organic group or a divalent to hexavalent alicyclic organic group.

$Y^1$ and $Y^2$ may be a residual group derived from a dicarboxylic acid or a residual group derived from a dicarboxylic acid derivative.

Examples of the dicarboxylic acid include without limitation $Y^1(COOH)_2$ or $Y^2(COOH)_2$ (wherein, $Y^1$ and $Y^2$ are the same as $Y^1$ and $Y^2$ of the above Chemical Formulas 12 and 13).

Examples of the carboxylic acid derivative include without limitation carbonyl halide derivatives of $Y^1(COOH)_2$, carbonyl halide derivatives of $Y^2(COOH)_2$, active compounds of an active ester derivative obtained by reacting $Y^1(COOH)_2$ with 1-hydroxy-1,2,3-benzotriazole, active compounds of an active ester derivative obtained by reacting $Y^2(COOH)_2$ with 1-hydroxy-1,2,3-benzotriazole (wherein $Y^1$ and $Y^2$ are the same as $Y^1$ and $Y^2$ of the above Chemical Formulas 12 and 13), and the like, and combinations thereof.

Examples of the dicarboxylic acid derivative include without limitation 4,4'-oxydibenzoylchloride, diphenyloxydicarbonyldichloride, bis(phenylcarbonylchloride)sulfone, bis(phenylcarbonylchloride)ether, bis(phenylcarbonylchloride)phenone, phthaloyldichloride, terephthaloyldichloride, isophthaloyldichloride, dicarbonyldichloride, diphenyloxydicarboxylatedibenzotriazole, and the like, and combinations thereof.

$Y^1$ and $Y^2$ may include a functional group represented by the following Chemical Formulas 21 to 23, but are not limited thereto.

[Chemical Formula 21]

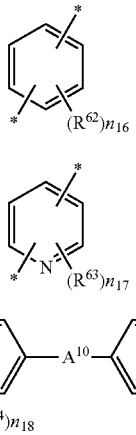

[Chemical Formula 22]

[Chemical Formula 23]

In Chemical Formulas 21 to 23, $R^{62}$ to $R^{65}$ are the same or different and are each independently hydrogen or substituted or unsubstituted alkyl, $n_{16}$ is an integer ranging from 1 to 4, $n_{17}$, $n_{18}$ and $n_{19}$ are the same or different and are independently an integer ranging from 1 to 3, and $A^{10}$ is O, $CR^{209}R^{210}$, CO, CONH, S, $SO_2$, or a single bond, wherein $R^{209}$ and $R^{210}$ are the same or different and are each independently hydrogen or substituted or unsubstituted alkyl, for example fluoroalkyl.

Further, the polybenzoxazole precursor may include a thermally polymerizable functional group at least one terminal end of the polybenzoxazole precursor.

The thermally polymerizable functional group links chains of a polymer through a thermal polymerization and lengthens chain length to increase the molecular weight of a polymer having a low molecular weight. The thermally polymerizable functional group is linked to a cross-linking agent through a cross-linking bond and thus can improve mechanical properties of a film.

The thermally polymerizable functional group may be derived from an end-capping monomer, for example, monoamines, monoanhydrides, monocarboxylic acid halides including a carbon-carbon multiple bond, and the like, and combinations thereof.

Examples of the monoamines include without limitation toluidine, dimethylaniline, ethylaniline, aminophenol, aminobenzylalcohol, aminoindan, aminoacetonephenone, and the like, and combinations thereof.

Examples of the monoanhydrides include without limitation 5-norbornene-2,3-dicarboxylanhydride represented by the following Chemical Formula 24, 3,6-epoxy-1,2,3,6-tetra hydrophthalicanhydride represented by the following Chemical Formula 25, isobutenyl succinic anhydride represented by the following Chemical Formula 26, maleic anhydride, aconitic anhydride, 3,4,5,6-tetrahydrophthalic anhydride, cis-1, 2,3,6,-tetrahydrophthalic anhydride, itaconic anhydride (IA), citraconic anhydride (CA), 2,3-dimethylmaleic anhydride (DMMA), and the like, and combinations thereof.

[Chemical Formula 24]

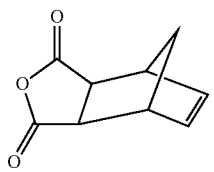

[Chemical Formula 25]

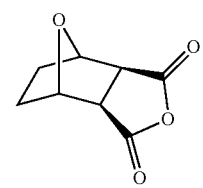

[Chemical Formula 26]

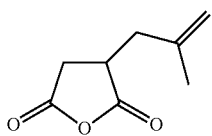

A thermally polymerizable functional group derived from the monoanhydrides includes a functional group represented by the following Chemical Formulas 27 to 30, but is not limited thereto. The thermally polymerizable functional group may be cross-linked during heating of the polybenzoxazole precursor preparation process, and may be formed as a residual group at the terminal end of the polybenzoxazole precursor.

[Chemical Formula 27]

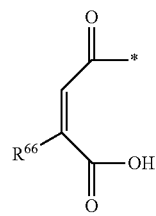

In Chemical Formula 27, $R^{66}$ is $CH_2COOH$ or $CH_2CHCHCH_3$.

[Chemical Formula 28]

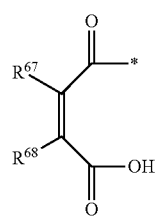

In Chemical Formula 28, $R^{67}$ and $R^{68}$ are the same or different and are each independently H or $CH_3$.

[Chemical Formula 29]

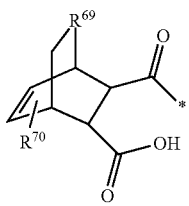

In Chemical Formula 29, $R^{69}$ is $CH_2$ or O, and $R^{70}$ is H or $CH_3$.

[Chemical Formula 30]

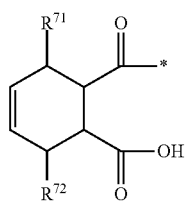

In Chemical Formula 30, $R^{71}$ and $R^{72}$ are the same or different and are each independently H, $CH_3$ or $OCOCH_3$.

The monocarboxylic acid halides including the carbon-carbon multiple bond may be represented by the following Chemical Formula 31.

[Chemical Formula 31]

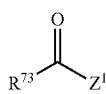

In Chemical Formula 31, $R^{73}$ is a substituted or unsubstituted alicyclic organic group or a substituted or unsubstituted aromatic organic group. The substituted alicyclic organic group or substituted aromatic organic group may be substituted with a substituent comprising a substituted or unsubstituted amidino group, a substituted or unsubstituted alicyclic organic group, or a fused ring of a substituted or unsubstituted alicyclic organic group with an aryl group. The substituted alicyclic organic group may be a maleimide group.

$Z^1$ is F, Cl, Br, or I.

Examples of the monocarboxylic acid halides including a carbon-carbon multiple bond include without limitation 5-norbornene-2-carboxylic acid halide represented by the following Chemical Formula 32, 4-nadimido benzoylhalide represented by the following Chemical Formula 33, 4-(4-phenylethynylphthalimido)benzoylhalide represented by the following Chemical Formula 34, 4-(2-phenylmaleicimido) benzoylhalide represented by the following Chemical Formula 35, benzoylhalide represented by the following Chemical Formula 36, cyclobenzoylhalide represented by the following Chemical Formula 37, 4-(3-phenylethynylphthalimido)benzoylhalide, 4-maleimido benzoylhalide, and the like, and combinations thereof.

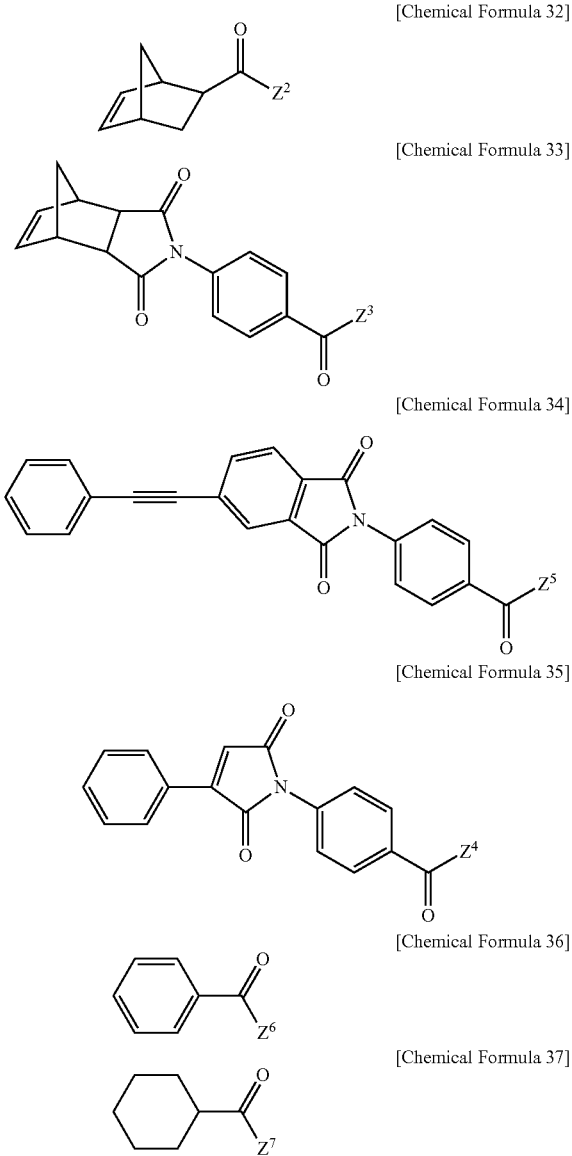

[Chemical Formula 32]

[Chemical Formula 33]

[Chemical Formula 34]

[Chemical Formula 35]

[Chemical Formula 36]

[Chemical Formula 37]

In Chemical Formulas 32 to 37, $Z^2$ to $Z^7$ are the same or different and are each independently F, Cl, Br, or I.

The polybenzoxazole precursor may have a weight average molecular weight (Mw) ranging from about 3000 to about 300,000. When the polybenzoxazole precursor has a weight average molecular weight within the above range, sufficient properties and excellent solubility in the organic solvent may be provided.

When the polybenzoxazole precursor includes a combination of a repeating unit represented by the above Chemical Formula 12 and a repeating unit represented by the above Chemical Formula 13, and the total amount of a repeating unit represented by above Chemical Formula 12 and a repeating unit represented by the above Chemical Formula 13 is 100 mol %, a repeating unit represented by above Chemical Formula 12 may be included in an amount ranging from about 60 mol % to about 95 mol % and a repeating unit represented by the above Chemical Formula 13 may be included in an amount ranging from about 5 mol % to about 40 mol %.

In some embodiments, the combination of a repeating unit represented by the above Chemical Formula 12 and a repeating unit represented by the above Chemical Formula 13 can include the repeating unit represented by the above Chemical Formula 12 in an amount of about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95 mol %. Further, according to some embodiments of the present invention, the amount of the repeating unit represented by the above Chemical Formula 12 can be in a range from about any of the foregoing amounts to about any other of the foregoing amounts.

In some embodiments, the combination of a repeating unit represented by the above Chemical Formula 12 and a repeating unit represented by the above Chemical Formula 13 can include the repeating unit represented by the above Chemical Formula 13 in an amount of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 mol %. Further, according to some embodiments of the present invention, the amount of the repeating unit represented by the above Chemical Formula 13 can be in a range from about any of the foregoing amounts to about any other of the foregoing amounts.

(B) Photosensitive Diazoquinone Compound

The photosensitive diazoquinone compound may be a compound including a 1,2-benzoquinone diazide or 1,2-naphtoquinone diazide structure.

Examples of the photosensitive diazoquinone compound may include a compound represented by the following Chemical Formulae 38 and 40 to 42, and combinations thereof, but is not limited thereto.

[Chemical Formula 38]

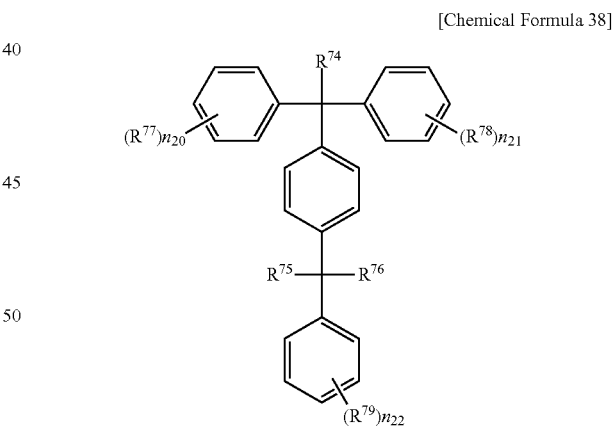

In Chemical Formula 38, $R^{74}$ to $R^{76}$ are the same or different and are each independently hydrogen or substituted or unsubstituted alkyl, for example $CH_3$, $R^{77}$ to $R^{79}$ are the same or different and are each independently OQ, wherein Q is hydrogen, the following Chemical Formula 39a or Chemical Formula 39b, provided that all Qs are not simultaneously hydrogen, and $n_{20}$ to $n_{22}$ are the same or different and are each independently integers ranging from 1 to 3.

[Chemical Formula 39a]

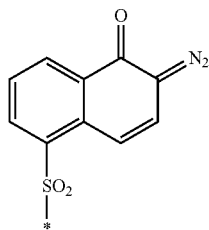

[Chemical Formula 39b]

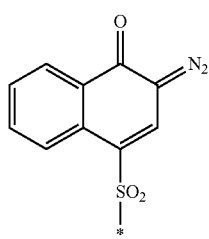

[Chemical Formula 40]

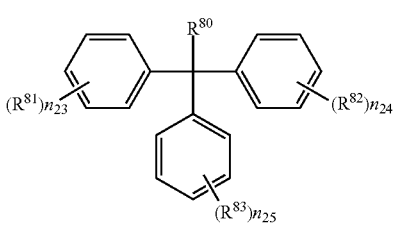

In Chemical Formula 40, $R^{80}$ is hydrogen or substituted or unsubstituted alkyl, $R^{81}$ to $R^{83}$ are OQ where Q is the same as defined in the above Chemical Formula 38, and $n_{23}$ to $n_{25}$ are the same or different and are each independently integers ranging from 1 to 3.

[Chemical Formula 41]

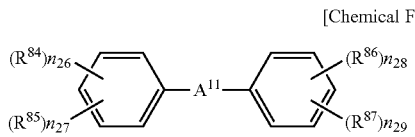

In Chemical Formula 41, $A^{11}$ is CO or $CR^{211}R^{212}$, wherein $R^{211}$ and $R^{212}$ are the same or different and are each independently substituted or unsubstituted alkyl, $R^{84}$ to $R^{87}$ are the same or different and are each independently hydrogen, substituted or unsubstituted alkyl, OQ or NHQ, wherein Q is the same as defined in the above Chemical Formula 38, $n_{26}$ to $n_{29}$ are the same or different and are independently integers ranging from 1 to 4, and $n_{26}+n_{27}$ and $n_{28}+n_{29}$ are the same or different and are independently integers of 5 or less, provided that at least one of $R^{84}$ and $R^{85}$ is OQ, and one aromatic ring includes one to three OQs and the other aromatic ring includes one to four OQs

[Chemical Formula 42]

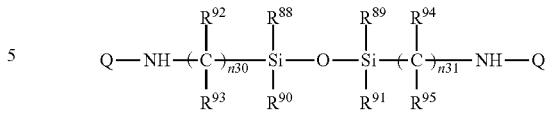

In Chemical Formula 42, $R^{88}$ to $R^{95}$ are the same or different and are each independently hydrogen or substituted or unsubstituted alkyl, $n_{30}$ and $n_{31}$ are the same or different and are each independently an integer ranging from 1 to 5, and each Q is the same or different and is the same as defined in the above Chemical Formula 38.

The positive photosensitive resin composition may include the photosensitive diazoquinone compound in an amount of about 5 to about 100 parts by weight based on about 100 parts by weight of the polybenzoxazole precursor. In some embodiments, the positive photosensitive resin composition may include the photosensitive diazoquinone compound in an amount of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 parts by weight. Further, according to some embodiments of the present invention, the amount of the photosensitive diazoquinone compound can be in a range from about any of the foregoing amounts to about any other of the foregoing amounts.

When the amount of the photosensitive diazoquinone compound is within the above range, the pattern can be well-formed without a residue from exposure, and film thickness loss during development can be minimized or prevented and thereby a good pattern can be provided.

(C) Phenol Compound

The positive photosensitive resin composition may include the above novel phenol compound.

That is, the phenol compound can include a compound represented by the above Chemical Formula 1, a compound represented by the above Chemical Formula 2, or a combination thereof.

In exemplary embodiments, the phenol compound may include one of the compounds represented by the above Chemical Formulas 3 to 11, or a combination thereof, but is not limited thereto.

Since the phenol compound includes the novel phenol compound, it can increase dissolution and sensitivity of exposed parts during development using an alkali aqueous solution for patterning and can play a role of forming high resolution patterns without residues (scum).

Since the novel phenol compound includes a large amount of hydroxy groups promoting dissolution compared with a conventional low molecular phenol compound, it may promote dissolution even in small amounts and thus can maintain the amount of a solid in a photosensitive resin composition and its viscosity within an appropriate range. In addition, the novel phenol compound can have low volatility and can remain during the curing and thus can bring about low film contraction rate, excellent resolution, pattern formation properties, and residue removal properties, and high elongation and tensile strength.

The novel phenol compound may include 2 to 30 hydroxy groups. When the novel phenol compound includes a number of hydroxy groups within the above range and is used for a positive photosensitive resin composition, it may be effectively dissolved in an alkali aqueous solution. In addition, the novel phenol compound may effectively improve sensitivity during the development. In exemplary embodiments, the novel phenol compound may include 3 to 20 hydroxy groups.

The positive photosensitive resin composition may include the novel phenol compound in an amount of about 1 to about 30 parts by weight based on about 100 parts by weight of the polybenzoxazole precursor. In some embodiments, the positive photosensitive resin composition may include the novel phenol compound in an amount of about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 parts by weight. Further, according to some embodiments of the present invention, the amount of the novel phenol compound can be in a range from about any of the foregoing amounts to about any other of the foregoing amounts.

When the novel phenol compound is included in an amount within the above range, sensitivity during development may be improved, and the dissolubility of the non-exposed part may be suitably increased to provide a good pattern and excellent residue removal properties. In addition, precipitation during freezing may not occur, so excellent storage stability can be realized.

In the positive photosensitive resin composition, the phenol compound may further include a generally-used phenol compound, besides the novel phenol compound.

The generally-used phenol compound may include a compound represented by one of the following Chemical Formulas 43 to 48, or a combination thereof, but is not limited thereto.

[Chemical Formula 43]

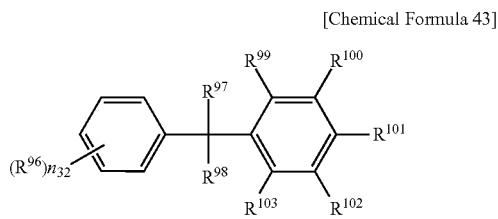

In Chemical Formula 43,
$R^{96}$ to $R^{98}$ are the same or different and are each independently hydrogen or substituted or unsubstituted alkyl,
$R^{99}$ to $R^{103}$ are the same or different and are each independently H, OH, or substituted or unsubstituted alkyl, for example the alkyl may be $CH_3$, and
$n_{32}$ is an integer ranging from 1 to 5.

[Chemical Formula 44]

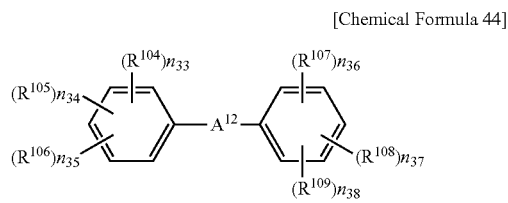

In Chemical Formula 44,
$R^{104}$ to $R^{109}$ are the same or different and are each independently H, OH, or substituted or unsubstituted alkyl,
$A^{12}$ is $CR^{213}R^{214}$ or a single bond, wherein $R^{213}$ and $R^{214}$ are the same or different and are each independently hydrogen or substituted or unsubstituted alkyl, for example the alkyl may be $CH_3$, $n_{33}$, $n_{34}$, $n_{35}$, $n_{36}$, $n_{37}$, and $n_{38}$ are the same or different and are each independently an integer ranging from 0 to 5, and
$n_{33}+n_{34}+n_{35}$ and $n_{36}+n_{37}+n_{38}$ are the same or different and are each independently an integer of 5 or less.

[Chemical Formula 45]

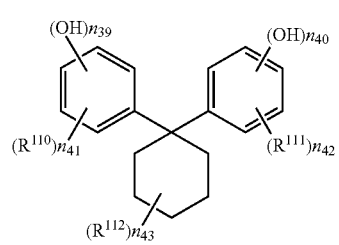

In Chemical Formula 45,
$R^{110}$ to $R^{112}$ are the same or different and are each independently hydrogen or substituted or unsubstituted alkyl,
$n_{39}$, $n_{40}$ and $n_{43}$ are the same or different and are each independently an integer ranging from 1 to 5, and
$n_{41}$ and $n_{42}$ are the same or different and are each independently an integer ranging from 0 to 4.

[Chemical Formula 46]

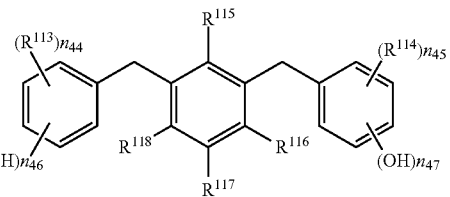

In Chemical Formula 46,
$R^{113}$ to $R^{118}$ are the same or different and are each independently hydrogen, OH, or substituted or unsubstituted alkyl,
$n_{44}$ to $n_{47}$ are the same or different and are each independently an integer ranging from 1 to 4, and
$n_{44}+n_{46}$ and $n_{45}+n_{47}$ are each independently an integer of 5 or less.

[Chemical Formula 48]

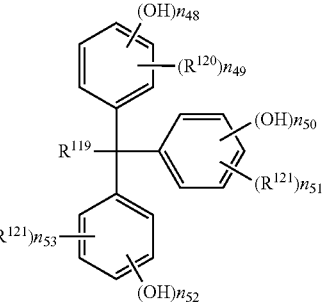

In Chemical Formula 47,
$R^{119}$ is substituted or unsubstituted alkyl, for example $CH_3$,
$R^{120}$ to $R^{122}$ are the same or different and are each independently hydrogen or substituted or unsubstituted alkyl,
$n_{48}$, $n_{50}$ and $n_{52}$ are the same or different and are each independently an integer ranging from 1 to 5, $n_{49}$, $n_{51}$ and $n_{53}$ are the same or different and are each independently an integer ranging from 0 to 4, and $n_{48}+n_{49}$, $n_{50}+n_{51}$ and $n_{52}+n_{53}$ are the same or different and are each independently an integer of 5 or less.

[Chemical Formula 48]

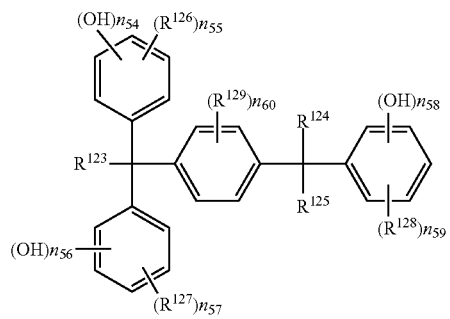

In Chemical Formula 48, $R^{123}$ to $R^{125}$ are the same or different and are each independently substituted or unsubstituted alkyl, for example $CH_3$, $R^{126}$ to $R^{129}$ are the same or different and are each independently hydrogen or substituted or unsubstituted alkyl, $n_{54}$, $n_{56}$ and $n_{58}$ are the same or different and are each independently an integer ranging from 1 to 5, $n_{55}$, $n_{57}$ and $n_{59}$ are the same or different and are each independently an integer ranging from 0 to 4, $n_{60}$ is an integer ranging from 1 to 4, and $n_{54}+n_{55}$, $n_{56}+n_{57}$ and $n_{58}+n_{59}$ are the same or different and are each independently an integer of 5 or less.

The positive photosensitive resin composition may include the conventional phenol compound in an amount of about 1 to about 30 parts by weight based on about 100 parts by weight of the polybenzoxazole precursor. In some embodiments, the positive photosensitive resin composition may include the conventional phenol compound in an amount of about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 parts by weight. Further, according to some embodiments, the amount of the conventional phenol compound can be in a range from about any of the foregoing amounts to about any other of the foregoing amounts.

(D) Silane Compound

The silane compound can improve adherence between the photosensitive resin composition and a substrate.

Examples of the silane compound may include without limitation a compound represented by the following Chemical Formulas 49 to 51, and combinations thereof; silane compounds including a carbon-carbon unsaturated bond such as vinyltrimethoxysilane, vinyltriethoxysilane, vinyltrichlorosilane, vinyltris(β-methoxyethoxy)silane; 3-methacryloxypropyltrimethoxysilane, 3-acryloxypropyltrimethoxysilane, p-styryltrimethoxysilane, 3-methacryloxypropylmethyldimethoxysilane, 3-methacryloxypropylmethyldiethoxysilane, trimethoxy[3-(phenylamino)propyl]silane, and the like, and combinations thereof.

[Chemical Formula 49]

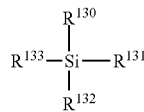

In Chemical Formula 49, $R^{130}$ is a vinyl group, substituted or unsubstituted alkyl, or substituted or unsubstituted aryl, for example 3-(meth)acryloxypropyl, p-styryl, or 3-(phenylamino)propyl, $R^{131}$ to $R^{133}$ are the same or different and are each independently substituted or unsubstituted alkoxy, substituted or unsubstituted alkyl, or halogen, and at least one of $R^{130}$ to $R^{133}$ is alkoxy or halogen, for example the alkoxy may be C1 to C8 alkoxy and the alkyl may be C1 to C20 alkyl.

[Chemical Formula 50]

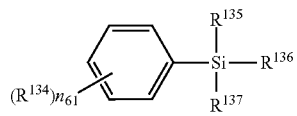

In Chemical Formula 50, $R^{134}$ is $NH_2$ or $CH_3CONH$, $R^{135}$ to $R^{137}$ are the same or different and are each independently substituted or unsubstituted alkoxy, for example $OCH_3$ or $OCH_2CH_3$, and $n_{61}$ is an integer ranging from 1 to 5.

[Chemical Formula 51]

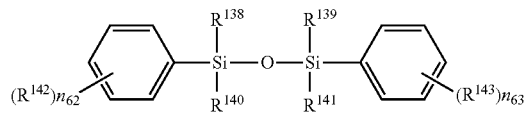

In Chemical Formula 51, $R^{138}$ to $R^{141}$ are the same or different and are each independently substituted or unsubstituted alkyl or substituted or unsubstituted alkoxy, for example $CH_3$ or $OCH_3$, $R^{142}$ and $R^{143}$ are the same or different and are each independently substituted or unsubstituted amino, for example $NH_2$ or $CH_3CONH$, and $n_{62}$ and $n_{63}$ are the same or different and are each independently an integer ranging from 1 to 5.

The positive photosensitive resin composition may include the silane compound in an amount of about 0.1 to about 30 parts by weight based on about 100 parts by weight of the polybenzoxazole precursor. In some embodiments, the positive photosensitive resin composition may include the silane compound in an amount of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, or parts by weight. Further, according to some embodiments of the present invention, the amount of the silane compound can be in a range from about any of the foregoing amounts to about any other of the foregoing amounts.

When the amount of the silane compound is within the above range, adherence between lower and upper layers may be improved, a residue film may not remain after development, and optical properties (transmittance), and mechanical properties such as tensile strength, elongation, and the like may be improved.

(E) Solvent

The solvent may be an organic solvent. Examples of the organic solvent include without limitation N-methyl-2-pyrrolidone, gamma-butyrolactone, N,N-dimethylacetate, dimethylsulfoxide, diethyleneglycoldimethylether, diethyleneglycoldiethylether, diethyleneglycoldibutylether, propyleneglycolmono methylether, dipropyleneglycolmonomethylether, propyleneglycolmonomethylether acetate, methyllactate, ethyllactate, butyllactate, methyl-1,3-butyleneglycolacetate, 1,3-butyleneglycol-3-monomethylether, methyl pyruvate, ethyl pyruvate, methyl-3-methoxy propionate, and the like, and combinations thereof. The solvent may be used singularly or in combination.

The positive photosensitive resin composition may include the solvent in an amount of about 50 to about 300 parts by weight based on about 100 parts by weight of the polybenzoxazole precursor. When the solvent is used in an amount within the above range, a sufficiently thick film can be obtained, and good solubility and coating can be provided.

(F) Other Additive(s)

The positive photosensitive resin composition may further include (F) one or more other additives.

An example of the other additives includes a latent thermal acid generator. Examples of the latent thermal acid generator include without limitation arylsulfonic acids such as p-toluenesulfonic acid and benzenesulfonic acid; perfluoroalkylsulfonic acids such as trifluoromethanesulfonic acid and trifluorobutanesulfonic acid; alkylsulfonic acids such as methanesulfonic acid, ethanesulfonic acid, and butanesulfonic acid; and the like, and combinations thereof.

The latent thermal acid generator is a catalyst for a dehydration reaction of the phenolic hydroxyl group-contained polyamide of the polybenzoxazole precursor and cyclization reaction, and thus a cyclization reaction can be performed smoothly even if curing temperature is decreased.

In addition, the positive photosensitive resin composition may further include an additive such as a suitable surfactant or leveling agent to prevent staining of the film or to improve development.

The process for forming a pattern using a positive photosensitive resin composition includes: coating a positive photosensitive resin composition on a supporting substrate; drying the coated positive photosensitive resin composition to provide a positive photosensitive resin composition layer; exposing the positive photosensitive resin composition layer; developing the positive photosensitive resin composition layer in an alkali aqueous solution to provide a photosensitive resin film; and heating the photosensitive resin film. The conditions of processes to provide a pattern are widely known in this art, so detailed descriptions thereof will be omitted in this specification.

According to another embodiment, a photosensitive resin film fabricated using the positive photosensitive resin composition is provided. The photosensitive resin film may be useful as an insulation layer or a protective layer.

According to further another embodiment, a semiconductor device including the photosensitive resin film is provided.

The photosensitive resin composition can be used as an insulation layer, a passivation layer, or a buffer coating layer in a semiconductor. The positive photosensitive resin composition may be used to form a surface protective layer or an interlayer insulating layer of a semiconductor device.

EXAMPLES

The following examples illustrate the present invention in more detail.

However, it is understood that the present invention is not limited by these examples.

Synthesis Example 1

Synthesis of Phenol Compound (P-1)

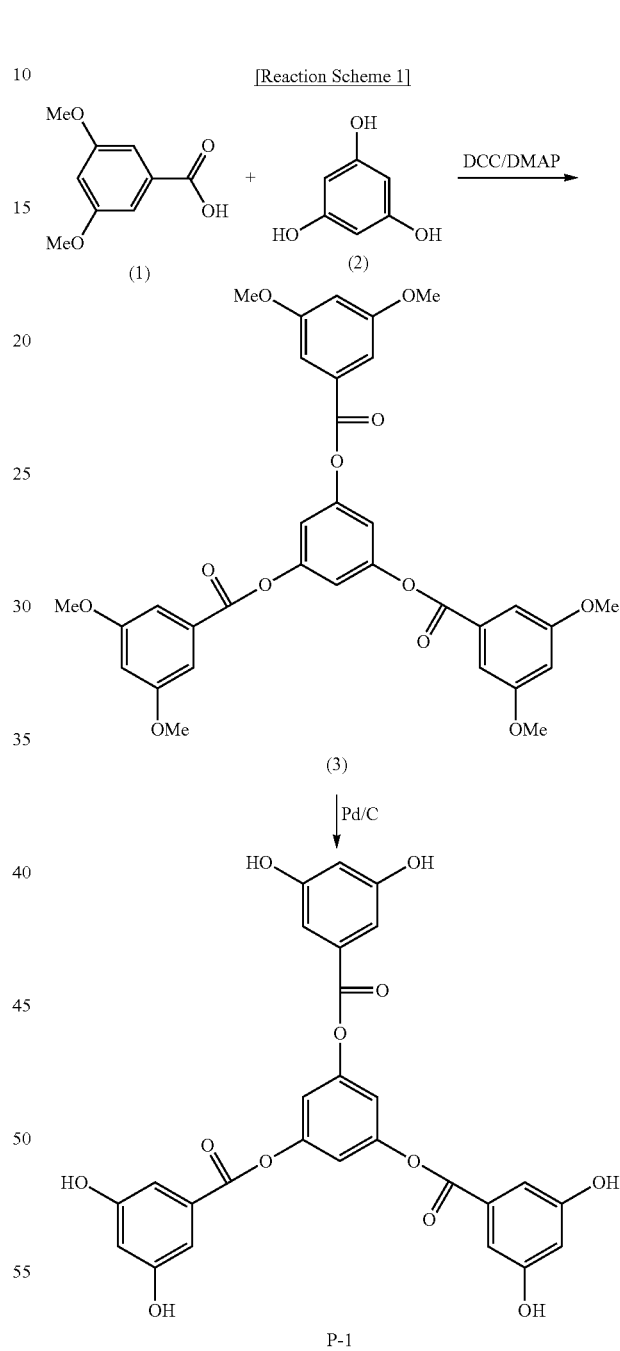

A phenol compound is synthesized according to the reaction scheme 1.

In particular, 10.0 g of 3,5-dimethoxybenzoic acid (1) is dissolved in a tetrahydrofuran (THF) solvent in a four-necked flask mounted with an agitator, a temperature controlling device, a nitrogen gas injector, and a condenser, while nitrogen is passed therethrough, and 2.31 g of 1,3,5-benzenetriol (2) is added thereto. The mixture is put in dicyclohexyl carbodiimide (DCC) and 4-dimethylaminopyridine (DMAP). Next, the resulting mixture is agitated for 6 hours at room temperature and vacuumed to remove the solvent, obtaining a compound (3). The compound (3) with 200 mg of 10% Pd/C and 300 mg of sodium carbonate is put in 30 ml of tetrahydrofuran for hydrogenation reaction. When the reaction is complete, the solvent is vacuumed and removed. The resulting product is recrystallized with diethylether and dichloromethane, preparing a phenol compound (P-1).

Synthesis Example 2

Synthesis of Phenol Compound (P-2)

[Reaction Scheme 2]

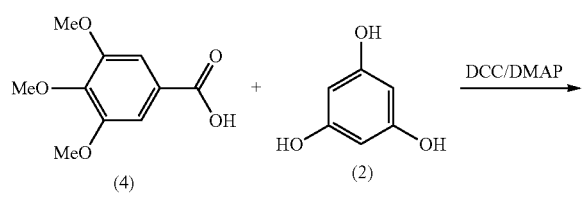

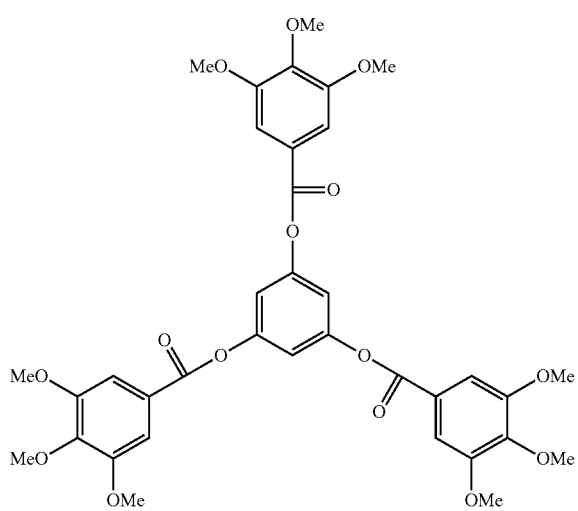

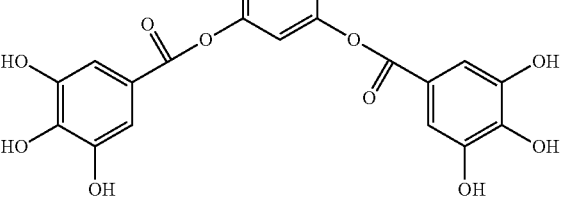

P-2

A phenol compound is synthesized according to the reaction scheme 2.

In particular, a phenol compound (P-2) is prepared according to the same method as Synthesis Example 1 except for using 3,4,5-trimethoxybenzoic acid (4) instead of 3,5-dimethoxybenzoic acid (1).

Synthesis Example 3

Synthesis of Phenol Compound (P-3)

A phenol compound (P-3) is prepared according to the same method as Synthesis Example 1 except for using 1,1,1-tris(4-hydroxyphenyl)ethane (6) instead of 1,3,5-benzenetriol (2).

[Chemical Formula P-3]

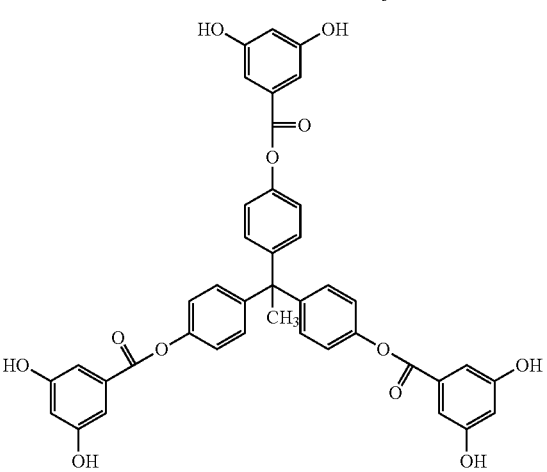

P-3

Synthesis Example 4

Synthesis of Phenol Compound (P-4)

A phenol compound (P-4) is prepared according to the same method as Synthesis Example 1 except for using 3,4,5- trimethoxybenzoic acid (4) instead of 3,5-dimethoxybenzoic acid (1) and 1,1,1-tris(4-hydroxyphenyl)ethane (6) instead of 1,3,5-benzenetriol (2).

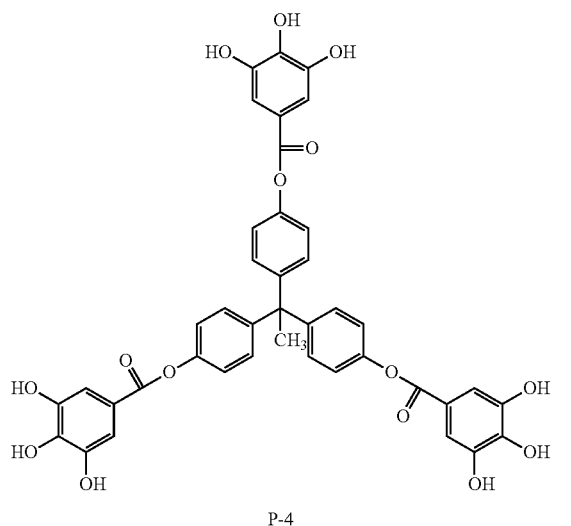

[Chemical Formula P-4]

P-4

Synthesis Example 5

Synthesis of Phenol Compound (P-5)

A phenol compound (P-5) is prepared according to the same method as Synthesis Example 1 except for using α,α,α'-tris (4-hydroxyphenyl)-1-ethyl-4-isopropylbenzene (7) instead of 1,3,5-benzenetriol (2).

[Chemical Formula P-5]

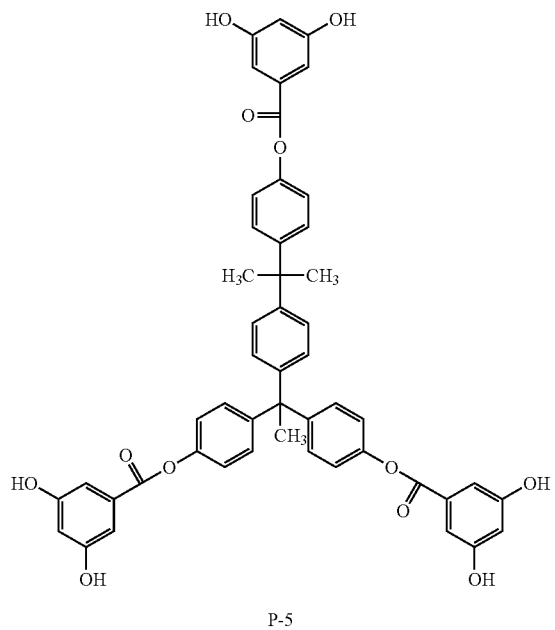

P-5

Synthesis Example 6

Synthesis of Phenol Compound (P-6)

A phenol compound (P-6) is prepared according to the same method as Synthesis Example 1 except for using 3,4,5-trimethoxybenzoic acid (4) instead of 3,5-dimethoxybenzoic acid (1) and α,α,α'-tris(4-hydroxyphenyl)-1-ethyl-4-isopropylbenzene (7) instead of 1,3,5-benzenetrio (2).

[Chemical Formula P-6]

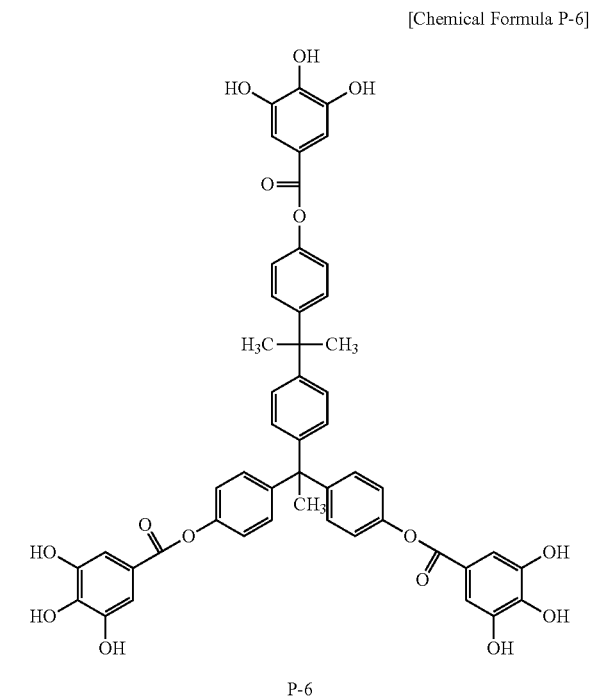

P-6

Synthesis Example 7

Synthesis of Polybenzoxazole Precursor (PBO-1)

17.4 g of 2,2-bis-amino-4-hydroxyphenyl)-1,1,1,3,3,3-hexafluoropropane and 0.86 g of 1,3-bis(aminopropyl)tetramethyldisiloxane are put in a four-necked flask mounted with an agitator, a temperature controlling device, a nitrogen gas injector, and a condenser, while nitrogen is passed therethrough, and 280 g of N-methyl-2-pyrrolidone (NMP) is added thereto to dissolve them therein.

When the solids are completely dissolved, 9.9 g of pyridine as a catalyst is added thereto. The mixture is maintained at a temperature ranging from 0° C. to 5° C., and a solution prepared by dissolving 13.3 g of 4,4'-oxydibenzoylchloride in 142 g of N-methyl-2-pyrrolidone (NMP) is slowly added thereto in a dropwise fashion for 30 minutes. The mixture is reacted for 1 hour at a temperature ranging from 0° C. to 5° C. and then, heated up to room temperature (about 25° C.) and agitated for one hour. Then, 1.6 g of 5-norbornene-2,3-dicarboxyanhydride is added to the agitated mixture. The resulting mixture is agitated at room temperature for 2 hours. The reaction mixture is poured into a solution prepared by mixing water/methanol in a volume ratio of 10/1, producing a precipitate. The precipitate is filtrated, sufficiently cleaned with water, and vacuum-dried at 80° C. for 24 hours, synthesizing a polybenzoxazole precursor (PBO-1). The polybenzoxazole precursor (PBO-1) has a weight average molecular weight of 9,800.

Synthesis Example 8

Synthesis of Polybenzoxazole Precursor (PBO-2)

17.4 g of 2,2-bis(3-amino-4-hydroxyphenyl)-1,1,1,3,3,3-hexafluoropropane is put in a four-necked flask mounted with an agitator, a temperature controlling device, a nitrogen gas injector, and a condenser, while nitrogen is passed therethrough, and 280 g of N-methyl-2-pyrrolidone (NMP) is added thereto to dissolve it.

When the solids are completely dissolved, 9.9 g of pyridine as a catalyst is added thereto. The mixture is maintained at a temperature ranging from 0° C. to 5° C., and a solution prepared by dissolving 13.3 g of 4,4'-oxydibenzoylchloride in 142 g of N-methyl-2-pyrrolidone (NMP) is slowly added thereto for 30 minutes in a dropwise fashion. The mixture is reacted for 1 hour at a temperature ranging from 0° C. to 5° C. and then, heated up to room temperature and agitated for one hour. Then, 1.6 g of 5-norbornene-2,3-dicarboxylanhydride is added to the agitated mixture. The resulting product is agitated at a room temperature for 2 hour. The resulting reactant is poured into a solution prepared by mixing water/methanol in a volume ratio of 10/1 to produce a precipitate. The precipitate is filtrated, sufficiently cleaned with water, and vacuum-dried at 80° C. for more than 24 hours, synthesizing a polybenzoxazole precursor (PBO-2). The polybenzoxazole precursor (PBO-2) has a weight average molecular weight of 9,650.

Example 1

Preparation of Positive Photosensitive Resin Composition 15 g of the polybenzoxazole precursor (PBO-1) according to Synthesis Example 7 is added to 35.0 g of γ-butyrolactone (GBL) and dissolved therein, and 3 g of photosensitive diazoquinone with a structure represented by the following Chemical Formula 38a, 0.75 g of trimethoxy[3-(phenylamino)propyl]silane represented by the following Chemical Formula 52 as a silane coupling agent, and 1.5 g of the phenol compound synthesized according to Synthesis Example 1 are added thereto and dissolved therein. The solution is filtrated with a 0.45 μm fluororesin filter, preparing a positive photosensitive resin composition.

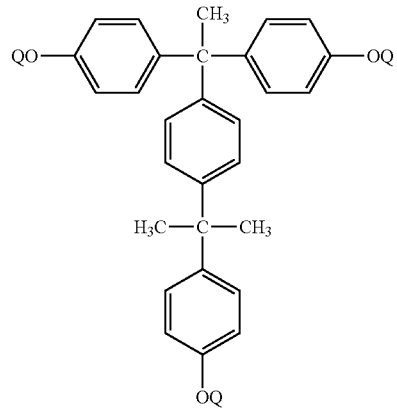

[Chemical Formula 38a]

In Chemical Formula 38a,
Q is the same as defined in the above Chemical Formula 38, and 67% of Q is substituted with the above Chemical Formula 39a.

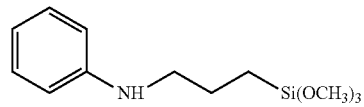

[Chemical Formula 52]

Example 2

Preparation of Positive Photosensitive Resin Composition

A positive photosensitive resin composition is prepared according to the same method as Example 1 except for using 1.5 g of the phenol compound according to Synthesis Example 2 instead of the phenol compound according to Synthesis Example 1.

Example 3

Preparation of Positive Photosensitive Resin Composition

A positive photosensitive resin composition is prepared according to the same method as Example 1 except for using 1.5 g of the phenol compound according to Synthesis Example 3 instead of the phenol compound according to Synthesis Example 1.

Example 4

Preparation of Positive Photosensitive Resin Composition

A positive photosensitive resin composition is prepared according to the same method as Example 1 except for using 1.5 g of the phenol compound according to Synthesis Example 4 instead of the phenol compound according to Synthesis Example 1.

Example 5

Preparation of Positive Photosensitive Resin Composition

A positive photosensitive resin composition is prepared according to the same method as Example 1 except for using 1.5 g of the phenol compound according to Synthesis Example 5 instead of the phenol compound according to Synthesis Example 1.

Example 6

Preparation of Positive Photosensitive Resin Composition

A positive photosensitive resin composition is prepared according to the same method as Example 1 except for using 1.5 g of the phenol compound according to Synthesis Example 6 instead of the phenol compound according to Synthesis Example 1.

Example 7

Preparation of Positive Photosensitive Resin Composition 15 g of the polybenzoxazole precursor (PBO-2) according to Synthesis Example 8 is added to 35.0 g of γ-butyrolactone (GBL) and dissolved therein, and 3 g of photosensitive diazoquinone represented by the above Chemical Formula 38a, 0.75 g of trimethoxy[3-(phenylamino)propyl]silane with a structure represented by the above Chemical Formula 52 as a silane coupling agent, and 1.5 g of the phenol compound according to Synthesis Example 1 are added thereto and dissolved therein. The solution is filtrated with a 0.45 μm fluororesin filter, preparing a positive photosensitive resin composition.

Example 8

Preparation of Positive Photosensitive Resin Composition

A positive photosensitive resin composition is prepared according to the same method as Example 7 except for using 1.5 g of the phenol compound according to Synthesis Example 2 instead of the phenol compound according to Synthesis Example 1.

Example 9

Preparation of Positive Photosensitive Resin Composition

A positive photosensitive resin composition is prepared according to the same method as Example 7 except for using 1.5 g of the phenol compound according to Synthesis Example 3 instead of the phenol compound according to Synthesis Example 1.

Example 10

Preparation of Positive Photosensitive Resin Composition

A positive photosensitive resin composition is prepared according to the same method as Example 7 except for using 1.5 g of the phenol compound according to Synthesis Example 4 instead of the phenol compound according to Synthesis Example 1.

Example 11

Preparation of Positive Photosensitive Resin Composition

A positive photosensitive resin composition is prepared according to the same method as Example 7 except for using 1.5 g of the phenol compound according to Synthesis Example 5 instead of the phenol compound according to Synthesis Example 1.

Example 12

Preparation of Positive Photosensitive Resin Composition

A positive photosensitive resin composition is prepared according to the same method as Example 7 except for using 1.5 g of the phenol compound according to Synthesis Example 6 instead of the phenol compound according to Synthesis Example 1.

Comparative Example 1

Preparation of Positive Photosensitive Resin Composition

A positive photosensitive resin composition is prepared according to the same method as Example 1 except for using 1.5 g of a phenol compound represented by the following Chemical Formula P-7 instead of the phenol compound according to Synthesis Example 1.

[Chemical Formula P-7]

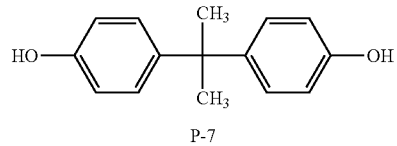

P-7

Comparative Example 2

Preparation of Positive Photosensitive Resin Composition

A positive photosensitive resin composition is prepared according to the same method as Example 1 except for using 1.5 g of a phenol compound represented by the following Chemical Formula P-8 instead of the phenol compound according to Synthesis Example 1.

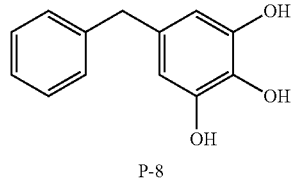

[Chemical Formula P-8]

P-8

Comparative Example 3

Preparation of Positive Photosensitive Resin Composition

A positive photosensitive resin composition is prepared according to the same method as Example 1 except for using 1.5 g of a phenol compound represented by the following Chemical Formula P-9 instead of the phenol compound according to Synthesis Example 1.

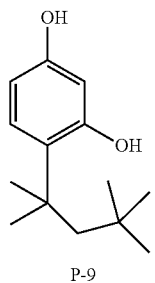

[Chemical Formula P-9]

P-9

The following Table 1 shows the compositions of the positive photosensitive resin compositions according to Examples 1 to 12 and Comparative Examples 1 to 3.

Experimental Example 1

Evaluation of Sensitivity, Resolution, and Residual Layer Rate

The positive photosensitive resin compositions according to Examples 1 to 12 and Comparative Examples 1 to 3 are respectively coated on a 8 inch wafer by using a spin-coater made by MIKASA Co., Ltd. (1H-DX2) and then, heated on a hot plate at 120° C. for 4 minutes, fabricating a photosensitive polybenzoxazole precursor film.

The photosensitive polybenzoxazole precursor films are exposed through a mask having various patterns by an I-line stepper (NSR i10C) manufactured by Japan Nikon for 250 ms, dissolved in a 2.38 wt % tetramethyl ammonium hydroxide aqueous solution at room temperature for 60 seconds (2 puddles) to remove the exposed part, and washed with pure water for 30 seconds. In addition, the obtained pattern is cured in an electric furnace under an oxygen concentration of 1000 ppm or below at 120° C. for 30 minutes and additionally at 320° C. for 1 hour to provide a patterned film.

In order to measure the sensitivity, the optimal exposure time is determined when a 10 μm L/S (line and space) pattern is formed in a line width of 1 to 1, and the resolution is determined as the minimum pattern size at the optimal exposure time. The results are shown in the following Table 2. The resolution is observed through an optical microscope.

Because film thickness loss after development affects the development and the resulting film thickness, it is desirable to decrease film thickness loss during development. In order to measure this, the pre-baked film is immersed in a 2.38 wt % tetramethyl ammonium hydroxide (TMAH) aqueous solution at different times and washed with water, so the change of film thickness is measured to calculate the residual film ratio (thickness after development/thickness before development, unit: %). The results are shown in the following Table 2. The film thickness change after pre-baking, development, and curing is measured by using ST4000-DLX equipment manufactured by KMAC Co.

TABLE 1

| | Polybenzoxazole precursor | | Solvent | | Photosensitive diazoquinone | | Silane compound | | Phenol compound | |
|---|---|---|---|---|---|---|---|---|---|---|
| | Kind | Amount (g) | Kind | Amount (g) | Used or not | Amount (g) | Used or not | Amount (g) | Kind | Amount (g) |
| Example 1 | PBO-1 | 15 | GBL | 35 | used | 3 | used | 0.75 | P-1 | 1.5 |
| Example 2 | PBO-1 | 15 | GBL | 35 | used | 3 | used | 0.75 | P-2 | 1.5 |
| Example 3 | PBO-1 | 15 | GBL | 35 | used | 3 | used | 0.75 | P-3 | 1.5 |
| Example 4 | PBO-1 | 15 | GBL | 35 | used | 3 | used | 0.75 | P-4 | 1.5 |
| Example 5 | PBO-1 | 15 | GBL | 35 | used | 3 | used | 0.75 | P-5 | 1.5 |
| Example 6 | PBO-1 | 15 | GBL | 35 | used | 3 | used | 0.75 | P-6 | 1.5 |
| Example 7 | PBO-2 | 15 | GBL | 35 | used | 3 | used | 0.75 | P-1 | 1.5 |
| Example 8 | PBO-2 | 15 | GBL | 35 | used | 3 | used | 0.75 | P-2 | 1.5 |
| Example 9 | PBO-2 | 15 | GBL | 35 | used | 3 | used | 0.75 | P-3 | 1.5 |
| Example 10 | PBO-2 | 15 | GBL | 35 | used | 3 | used | 0.75 | P-4 | 1.5 |
| Example 11 | PBO-2 | 15 | GBL | 35 | used | 3 | used | 0.75 | P-5 | 1.5 |
| Example 12 | PBO-2 | 15 | GBL | 35 | used | 3 | used | 0.75 | P-6 | 1.5 |
| Comparative Example 1 | PBO-1 | 15 | GBL | 35 | used | 3 | used | 0.75 | P-7 | 1.5 |
| Comparative Example 2 | PBO-1 | 15 | GBL | 35 | used | 3 | used | 0.75 | P-8 | 1.5 |
| Comparative Example 3 | PBO-1 | 15 | GBL | 35 | used | 3 | used | 0.75 | P-9 | 1.5 |

TABLE 2

|  | Phenol | Film thickness (μm) pre-baking | After development | Change of film thickness during development (μm) | Sensitivity (mJ/cm$^2$) | Resolution (μm) |
|---|---|---|---|---|---|---|
| Example 1 | P-1 | 10.6 | 9.4 | 1.2 | 390 | 2 |
| Example 2 | P-2 | 10.3 | 9.1 | 1.2 | 350 | 3 |
| Example 3 | P-3 | 9.8 | 8.7 | 1.1 | 380 | 4 |
| Example 4 | P-4 | 10.4 | 9.3 | 1.1 | 350 | 4 |
| Example 5 | P-5 | 10.0 | 8.8 | 1.2 | 400 | 3 |
| Example 6 | P-6 | 9.8 | 8.6 | 1.2 | 400 | 3 |
| Example 7 | P-1 | 10.2 | 9.2 | 1.0 | 350 | 3 |
| Example 8 | P-2 | 10.0 | 8.5 | 1.5 | 380 | 3 |
| Example 9 | P-3 | 10.2 | 8.7 | 1.6 | 350 | 2 |
| Example 10 | P-4 | 10.1 | 8.8 | 1.3 | 400 | 3 |
| Example 11 | P-5 | 10.2 | 8.7 | 1.5 | 370 | 4 |
| Example 12 | P-6 | 10.0 | 8.7 | 1.3 | 350 | 3 |
| Comparative Example 1 | P-7 | 9.8 | 7.6 | 2.2 | 500 | 5 |
| Comparative Example 2 | P-8 | 9.9 | 7.8 | 2.1 | 510 | 7 |
| Comparative Example 3 | P-9 | 9.5 | 7.6 | 1.9 | 500 | 5 |

Referring to Table 2, the positive photosensitive resin compositions including a polybenzoxazole precursor including a novel phenol compound including plenty of hydroxy groups according to Examples 1 to 12 have remarkably better sensitivity but less thickness decrease after the curing than the ones according to Comparative Examples 1 to 3 and have excellent photo properties such as resolution, thickness decrease during the development, and the like.

Based on the above results, a positive photosensitive resin composition according to one embodiment is found to form a semiconductor insulation layer or a protective layer with excellent performance through more efficient patterning than a positive photosensitive resin composition including a conventional phenol compound. In addition, a semiconductor insulation layer or a protective layer formed of a positive photosensitive resin composition according to one embodiment is found to have excellent performance compared with a semiconductor protective layer formed of a conventional positive photosensitive resin composition in terms of mechanical properties.

Many modifications and other embodiments of the invention will come to mind to one skilled in the art to which this invention pertains having the benefit of the teachings presented in the foregoing descriptions. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation, the scope of the invention being defined in the claims.

What is claimed is:

1. A positive photosensitive resin composition, comprising:
   (A) a polybenzoxazole precursor including a repeating unit represented by the following Chemical Formula 12, a repeating unit represented by the following Chemical Formula 13, or a combination thereof, and a thermally polymerizable functional group at least one terminal end of the polybenzoxazole precursor;
   (B) a photosensitive diazoquinone compound;
   (C) a phenol compound comprising a compound represented by the following Chemical Formula 1, a compound represented by the following Chemical Formula 2, or a combination thereof:

[Chemical Formula 1]

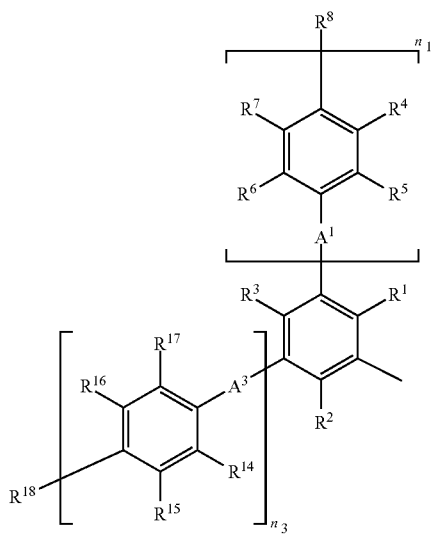

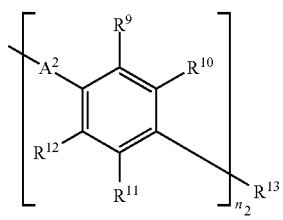

-continued

[Chemical Formula 2]

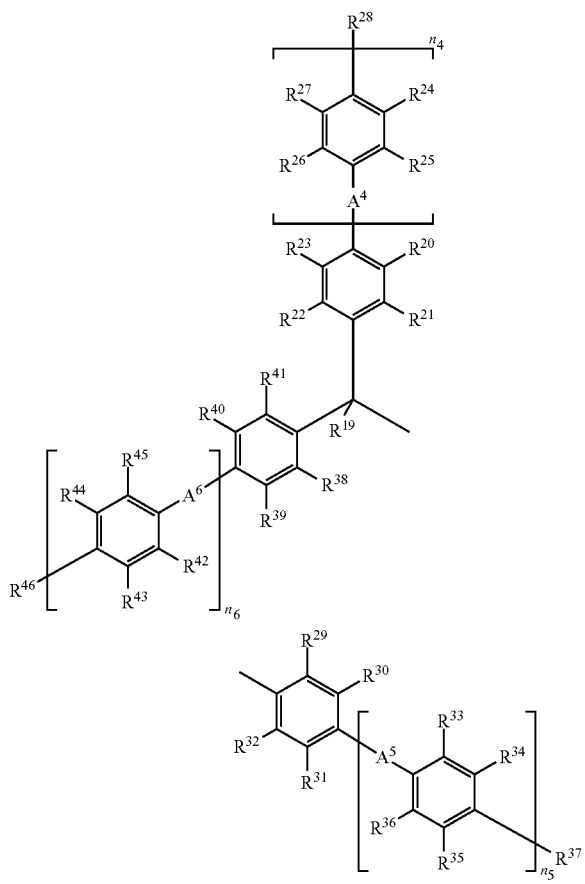

wherein, in Chemical Formulas 1 and 2, $R^1$ to $R^{46}$ are the same or different and are each independently hydrogen, hydroxyl, a substituted or unsubstituted C1 to C30 aliphatic organic group, substituted or unsubstituted C1 to C30 alkoxy, or halogen, provided that at least one of $R^1$ to $R^{46}$ is hydroxy, $A^1$ to $A^3$ are the same or different and are each independently O, CO, COO, $SO_2$, S, CONH (amide bond), $CH_2O$ or a single bond, $A^4$ to $A^6$ are the same or different and are each independently O, CO, COO, $CR_{203}R_{204}$, $SO_2$, S, CONH (amide bond), $CH_2O$ or a single bond, wherein $R_{203}$ and $R_{204}$ are the same or different and are each independently hydrogen or a substituted or unsubstituted C1 to C30 aliphatic organic group, and n1 to n6 are the same or different and are each independently an integer ranging from 1 to 5;

(D) a silane compound; and (E) a solvent:

[Chemical Formula 12]

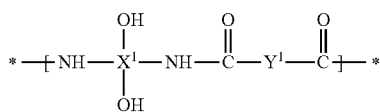

-continued

[Chemical Formula 13]

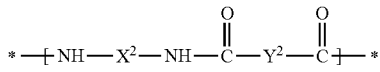

wherein, in Chemical Formulas 12 and 13, $X^1$ is an aromatic organic group, $X^2$ is an aromatic organic group, a divalent to hexavalent alicyclic organic group, or a functional group represented by the following Chemical Formula 14, and, $Y^1$ and $Y^2$ are the same or different and are independently an aromatic organic group or a divalent to hexavalent alicyclic organic group,

[Chemical Formula 14]

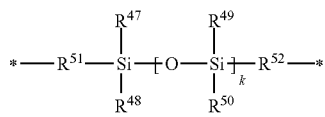

wherein, in Chemical Formula 14, $R^{47}$ to $R^{50}$ are the same or different and are each independently substituted or unsubstituted alkyl, substituted or unsubstituted aryl, substituted or unsubstituted alkoxy, or hydroxy, $R^{51}$ and $R^{52}$ are the same or different and are each independently substituted or unsubstituted alkylene or substituted or unsubstituted arylene, and k is an integer ranging from 1 to 50.

2. The positive photosensitive resin composition of claim 1, wherein the thermally polymerizable functional group is derived from a reactive end-capping monomer comprising a monoamine, a monoanhydride, a mono carboxylic acid halide including a carbon-carbon multiple bond, or a combination thereof.

3. The positive photosensitive resin composition of claim 2, wherein the monoamine comprises toluidine, dimethylaniline, ethylaniline, aminophenol, aminobenzylalcohol, aminoindan, aminoacetophenone, or a combination thereof.

4. The positive photosensitive resin composition of claim 2, wherein the monoanhydride comprises 5-norbornene-2,3-dicarboxylanhydride represented by the following Chemical Formula 24, 3,6-epoxy-1,2,3,6-tetra hydrophthalicanhydride represented by the following Chemical Formula 25, isobutenyl succinic anhydride represented by the following Chemical Formula 26, maleic anhydride, aconitic anhydride, 3,4,5,6-tetrahydrophthalic anhydride, cis-1,2,3,6,-tetrahydrophthalic anhydride, itaconic anhydride (IA), citraconic anhydride (CA), 2,3-dimethylmaleic anhydride (DMMA), or a combination thereof.

[Chemical Formula 24]

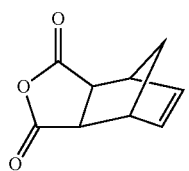

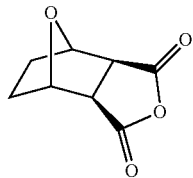
[Chemical Formula 25]

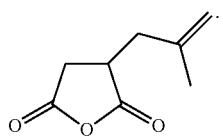
[Chemical Formula 26]

5. The positive photosensitive resin composition of claim 2, wherein the monocarboxylic acid halide including a carbon-carbon multiple bond is represented by following Chemical Formula 31:

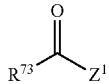
[Chemical Formula 31]

wherein, in Chemical Formula 31,
R$^{73}$ is a substituted or unsubstituted alicyclic organic group or a substituted or unsubstituted aromatic organic group, and
Z$^1$ is F, Cl, Br, or I.

6. The positive photosensitive resin composition of claim 5, wherein the monocarboxylic acid halide including a carbon-carbon multiple bond comprises 5-norbornene-2-carboxylic acid halide represented by the following Chemical Formula 32, 4-nadimido benzoylhalide represented by the following Chemical Formula 33, 4-(4-phenylethynylphthalimido)benzoylhalide represented by the following Chemical Formula 34, 4-(2-phenylmaleicimido)benzoylhalide represented by the following Chemical Formula 35, benzoylhalide represented by the following Chemical Formula 36, cyclobenzoylhalide represented by the following Chemical Formula 37, 4-(3-phenylethynylphthalimido)benzoylhalide, 4-maleimido benzoylhalide, or a combination thereof:

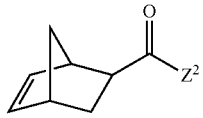
[Chemical Formula 32]

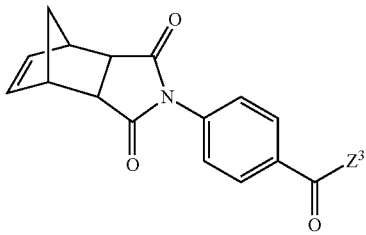
[Chemical Formula 33]

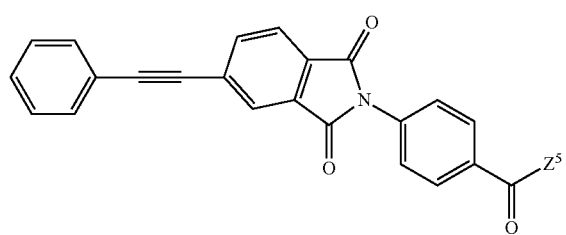
[Chemical Formula 34]

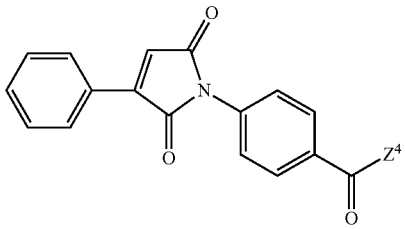
[Chemical Formula 35]

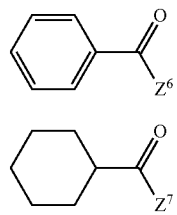
[Chemical Formula 36]

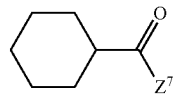
[Chemical Formula 37]

wherein, in Chemical Formulas 32 to 37,
Z$^2$ to Z$^7$ are the same or different and are each independently F, Cl, Br, or I.

7. The positive photosensitive resin composition of claim 1, wherein when the polybenzoxazole precursor comprises a combination of a repeating unit represented by the above Chemical Formula 12 and a repeating unit represented by the above Chemical Formula 13, and the total amount of a repeating unit represented by above Chemical Formula 12 and a repeating unit represented by the above Chemical Formula 13 is 100 mol %, a repeating unit represented by above Chemical Formula 12 is included in an amount ranging from about 60 mol % to about 95 mol % and a repeating unit represented by the above Chemical Formula 13 is included in an amount ranging from about 5 mol % to about 40 mol %.

8. The positive photosensitive resin composition of claim 1, wherein the polybenzoxazole precursor has a weight average molecular weight (Mw) ranging from about 3000 to about 300,000.

9. The positive photosensitive resin composition of claim 1, wherein the positive photosensitive resin composition comprises
about 5 to about 100 parts by weight of the photosensitive diazoquinone compound (B),
about 1 to about 30 parts by weight of the phenol compound (C),
about 0.1 to about 30 parts by weight of the silane compound (D), and
about 50 to about 300 parts by weight of the solvent (E),
wherein the amount of (B), (C), (D) and (E) is based on about 100 parts by weight of the polybenzoxazole precursor (A).

10. A photosensitive resin film fabricated using the positive photosensitive resin composition of claim 1.

11. A semiconductor device including the photosensitive resin film of claim 10.

12. The positive photosensitive resin composition of claim 1, wherein the phenol compound comprises a compound represented by Chemical Formula 1, wherein at least one of $A^1$ to $A^3$ is COO.

13. The positive photosensitive resin composition of claim 1, wherein the phenol compound comprises a compound represented by Chemical Formula 1, wherein each of $A^1$ to $A^3$ is COO.

14. The positive photosensitive resin composition of claim 1, wherein the phenol compound comprises a compound represented by Chemical Formula 2, wherein at least one of $A^4$ to $A^6$ is COO.

15. The positive photosensitive resin composition of claim 1, wherein the phenol compound comprises 2 to 30 hydroxy groups.

16. The positive photosensitive resin composition of claim 1, wherein the phenol compound comprises a compound represented by one of the following Chemical Formulas 3 to 11 or a combination thereof:

[Chemical Formula 3]

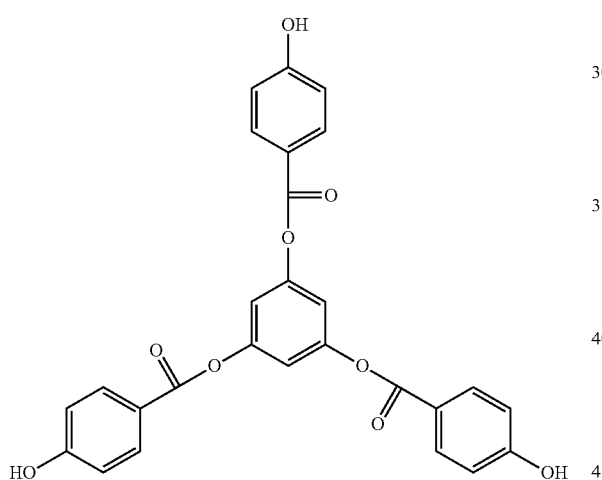

[Chemical Formula 4]

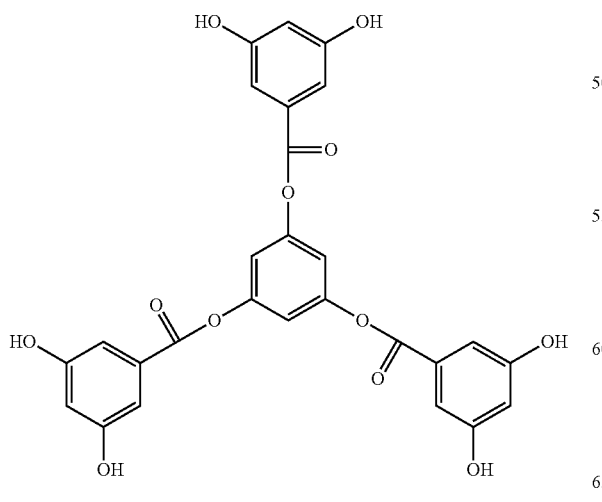

[Chemical Formula 5]

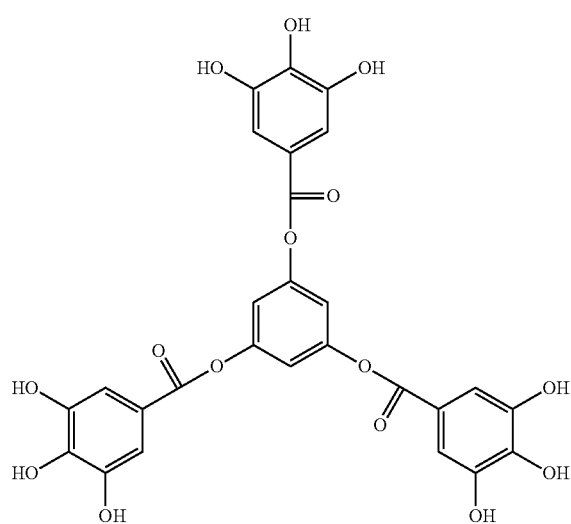

[Chemical Formula 6]

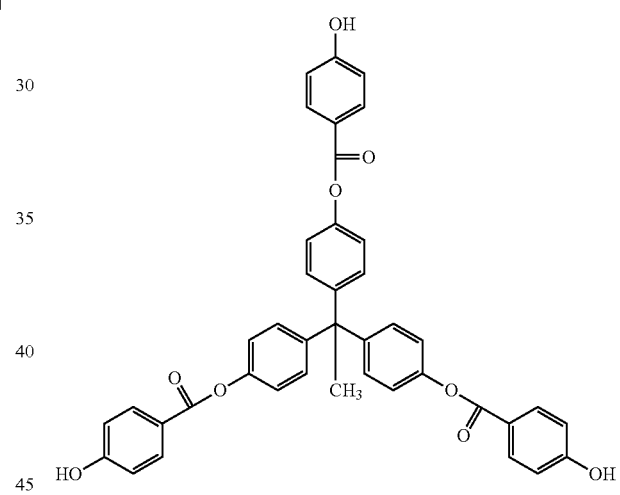

[Chemical Formula 7]

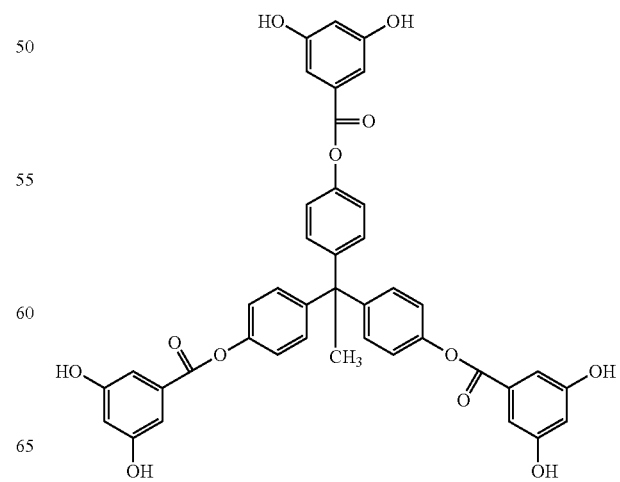

[Chemical Formula 8]
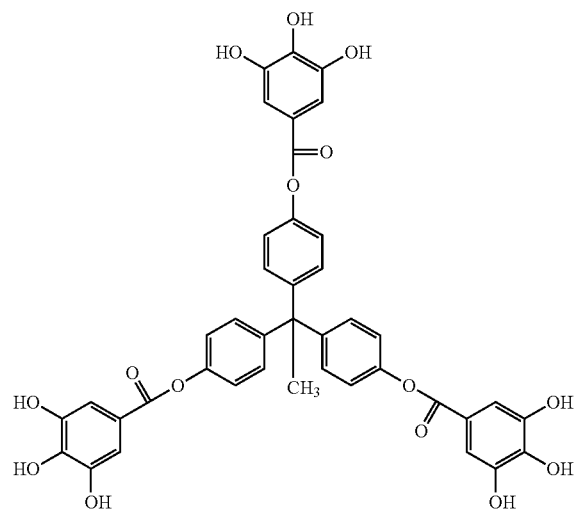
[Chemical Formula 9]
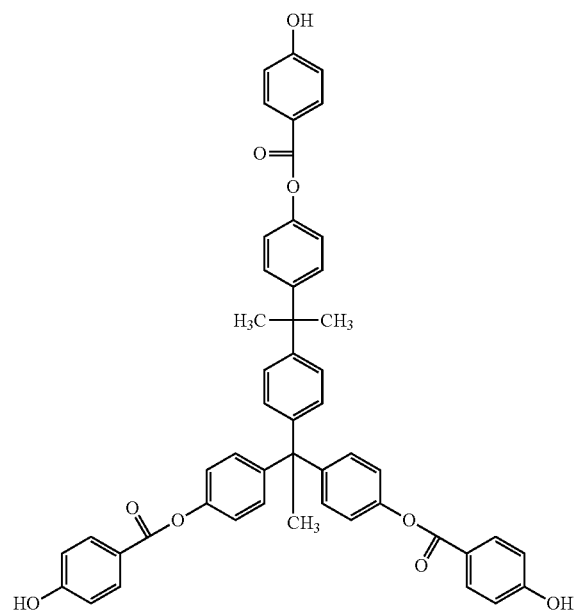
[Chemical Formula 10]
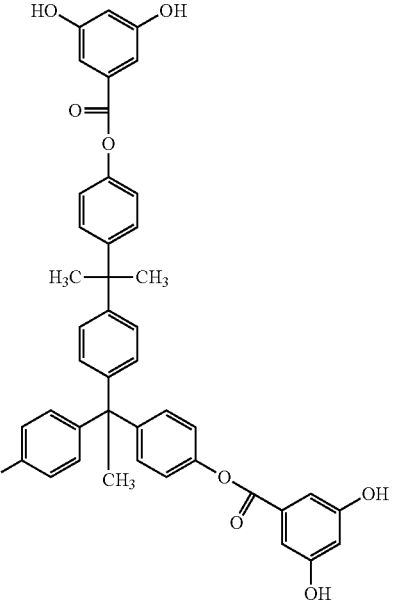
[Chemical Formula 11]
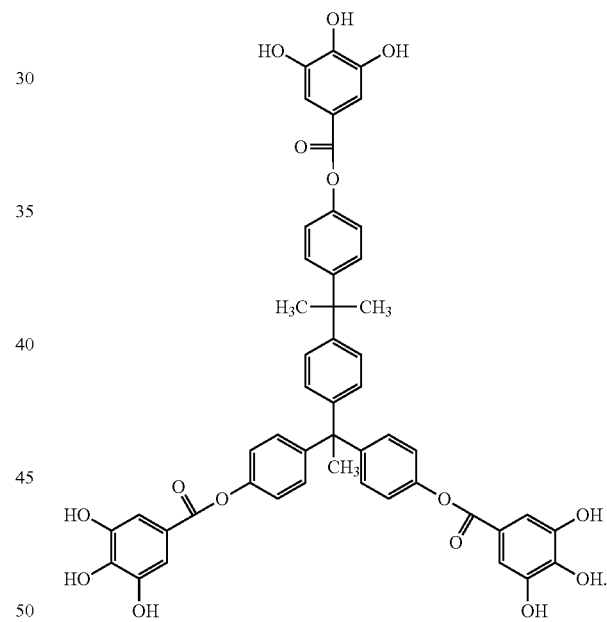
* * * * *

UNITED STATES PATENT AND TRADEMARK OFFICE
CERTIFICATE OF CORRECTION

PATENT NO.      : 8,697,320 B2                                Page 1 of 1
APPLICATION NO. : 13/242120
DATED           : April 15, 2014
INVENTOR(S)     : Ji-Young Jeong et al.

It is certified that error appears in the above-identified patent and that said Letters Patent is hereby corrected as shown below:

In the Specification

Column 30, Line 49 reads: [Chemical Formula 48] and should read: [Chemical Formula 47]

Column 32, Line 57 reads: "17, 18, 19, 20, 21, 22, 23, 24, 25, 26, 27, 28, 29, or parts by" and should read: "17, 18, 19, 20, 21, 22, 23, 24, 25, 26, 27, 28, 29, or 30 parts by"

Signed and Sealed this
Fifteenth Day of July, 2014

Michelle K. Lee
*Deputy Director of the United States Patent and Trademark Office*